US 6,576,008 B2

(12) United States Patent
Devonec et al.

(10) Patent No.: US 6,576,008 B2
(45) Date of Patent: Jun. 10, 2003

(54) METHODS AND DEVICE FOR INSERTING AND WITHDRAWING A TWO PIECE STENT ACROSS A CONSTRICTING ANATOMIC STRUCTURE

(75) Inventors: Marian A. Devonec, Miribel (FR); Robert F. Rioux, Ashland, MA (US); Kimberly A. Paddock, Newton, MA (US); John W. Lehman, Wayland, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/899,112

(22) Filed: Jul. 6, 2001

(65) Prior Publication Data

US 2002/0128705 A1 Sep. 12, 2002

Related U.S. Application Data

(60) Continuation-in-part of application No. 09/032,978, filed on Mar. 2, 1998, now Pat. No. 6,290,666, which is a division of application No. 08/501,140, filed as application No. PCT/FR94/00171 on Feb. 16, 1994, now Pat. No. 5,766,209.

(30) Foreign Application Priority Data

Feb. 19, 1993 (FR) .............................. 93 02284

(51) Int. Cl.[7] ................................. A61F 2/06
(52) U.S. Cl. .................... 623/1.16; 623/23.64
(58) Field of Search .................. 604/8; 623/1.11, 623/1.12, 1.16, 23.64–23.66, 23.7

(56) References Cited

U.S. PATENT DOCUMENTS 3,527,226 A  9/1970 Hakin (List continued on next page.)

FOREIGN PATENT DOCUMENTS

| EP | 0 341 988 B1 | 1/1993 |
| FR | 2 667 783 | 4/1992 |
| WO | 91 16005 | 10/1991 |

OTHER PUBLICATIONS

William R. Fair, "Internal Urethrotomy without a catheter: Use of a Urethral Stent" *The Journal of Urology*, vol. 127, pp. 675–676, Apr. 1982.

R. Robert De Nicola, "Permanent Artificial (Silicone) Urethra", *The Journal of Urology*, vol. 63, No. 1 pp. 168–172, (1950).

L.A. Loizou, M.D. et al., "Treatment of Malignant Structures of the Cervical Esophagus by Endoscopic Intubation Using Modified Endoprostheses", *Gastrointestinal Endoscopy*, pp. 158–164, (1992).

The TITAN Ontra–Prostatic Stent, Advanced Surgical Intervention, Inc.

(List continued on next page.)

*Primary Examiner*—David H. Willse
*Assistant Examiner*—Mavier G. Blanco
(74) *Attorney, Agent, or Firm*—Oliff & Berridge, PLC

(57) ABSTRACT

A stent device and methods for inserting and removing a stent to and from an anatomical tract of a living being. The stent includes a distal segment and a proximal segment joined by a flexible connection structure. The stent is inserted using components comprising a delivery assembly such that the stent proceeds through the anatomical tract and seats the flexible connection structure of the stent in a natural constricting structure of the anatomical tract. The flexible quality of the connection structure permits the natural constricting functions of the anatomical tract to occur. The natural closure of the anatomical constricting structure stops the flow of fluid, for example, from a target organ which indicates that the stent is properly placed within the anatomical tract.

46 Claims, 29 Drawing Sheets

U.S. PATENT DOCUMENTS

| | | |
|---|---|---|
| 3,657,744 A | 4/1972 | Ersek |
| 3,938,529 A | 2/1976 | Gibbons |
| 4,240,434 A | 12/1980 | Newkirk |
| 4,350,161 A | 9/1982 | Davis, Jr. |
| 4,423,725 A | 1/1984 | Baran et al. |
| 4,432,757 A | 2/1984 | Davis, Jr. |
| 4,768,507 A | 9/1988 | Fischell et al. |
| 4,895,566 A | 1/1990 | Lee |
| 4,973,301 A | 11/1990 | Nissenkorn |
| 4,990,155 A | 2/1991 | Wilkoff |
| 5,059,169 A | 10/1991 | Zilber |
| 5,078,720 A | 1/1992 | Burton et al. |
| 5,098,374 A | 3/1992 | Othel-Jacobsen et al. |
| 5,116,309 A * | 5/1992 | Coll ............................ 604/8 |
| 5,122,154 A | 6/1992 | Rhodes |
| 5,152,749 A | 10/1992 | Giesy et al. |
| 5,176,625 A | 1/1993 | Brisson |
| 5,176,626 A | 1/1993 | Soehendra |
| 5,222,971 A | 6/1993 | Willard et al. |
| 5,234,456 A | 8/1993 | Silvestrini |
| 5,258,020 A | 11/1993 | Froix |
| 5,282,784 A | 2/1994 | Willard |
| 5,282,823 A | 2/1994 | Schwartz et al. |
| 5,292,802 A | 3/1994 | Rhee et al. |
| 5,419,760 A | 5/1995 | Narciso |
| 5,429,634 A | 7/1995 | Narciso |
| 5,514,112 A | 5/1996 | Chu et al. |
| 5,514,178 A | 5/1996 | Torchio |
| 5,736,127 A | 4/1998 | Stoy et al. |
| 5,766,209 A | 6/1998 | Devonec |
| 5,792,400 A | 8/1998 | Talja et al. |
| 5,830,179 A * | 11/1998 | Mikus et al. .................. 604/49 |
| 5,876,417 A * | 3/1999 | Devonec et al. ............. 606/182 |
| 5,971,967 A * | 10/1999 | Willard ....................... 604/264 |
| 6,022,312 A * | 2/2000 | Chaussy et al. ............... 600/29 |
| 6,238,368 B1 | 5/2001 | Devonec |

OTHER PUBLICATIONS

UltraFlex Urethral Stent System, Micrvasive Boston Scientific Corporation.
Memotherm Urethral Stents, angiomed.
Intraurethral Catheter, angiomed.
Barnes Stent, Bard.
Urocoil, Prostacoil, Almed.
Prostalcath, Pharma–Plast A/S.
Variospire, Laboratoires Bruneau.
Uromed, Urologishe Spirale, Uromedical–Products.
La Spirale, Porges.

* cited by examiner

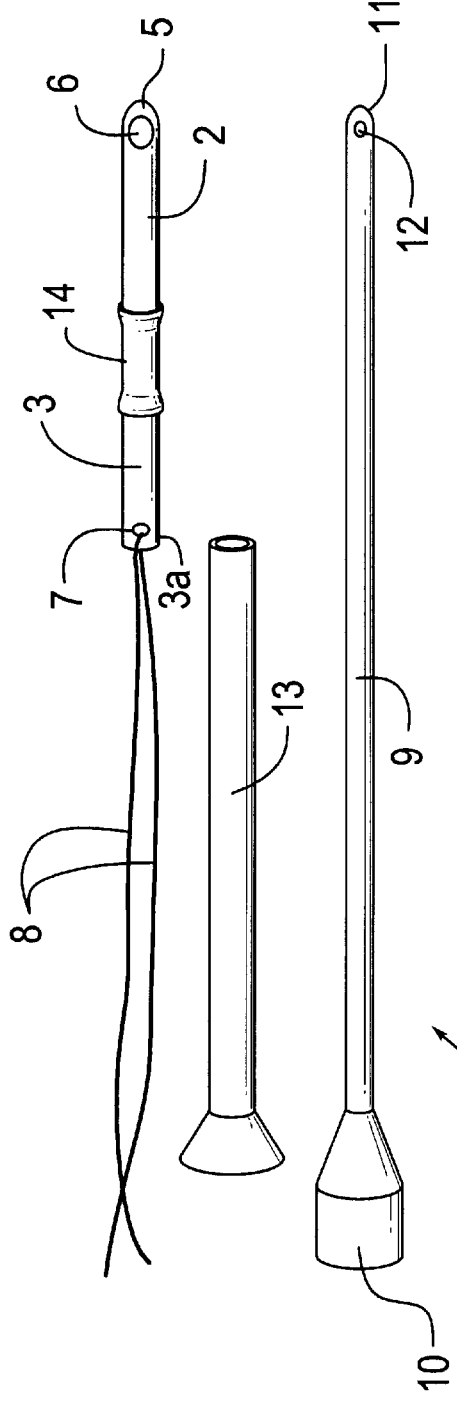
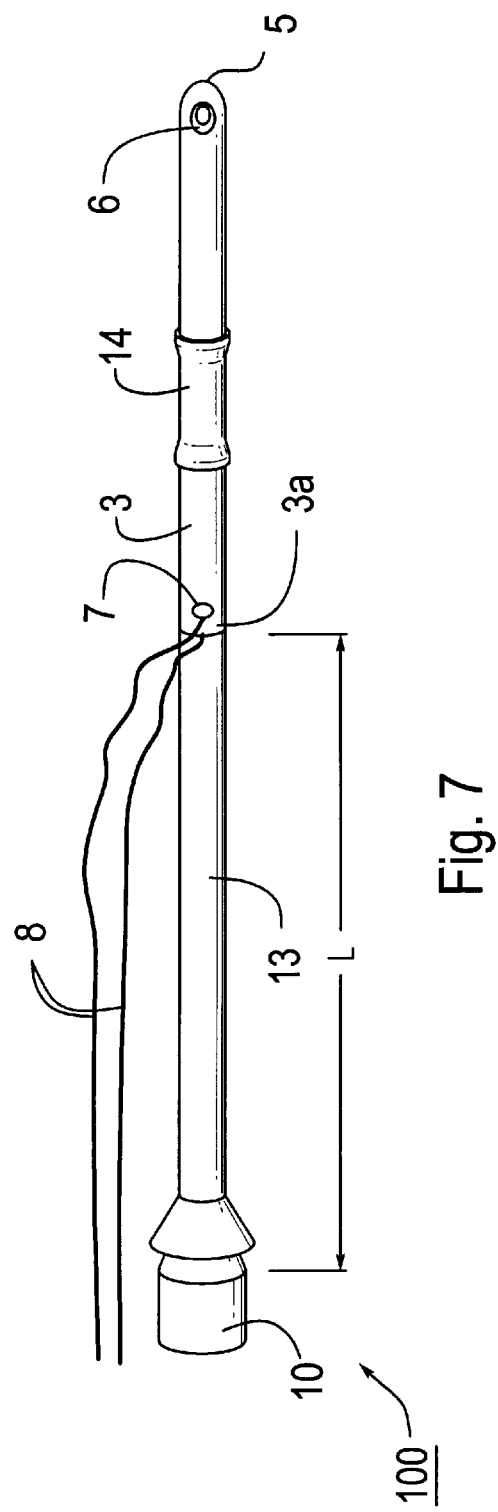

ND DEVICE FOR INSERTING
METHODS AND DEVICE FOR INSERTING AND WITHDRAWING A TWO PIECE STENT ACROSS A CONSTRICTING ANATOMIC STRUCTURE

This is a Continuation in Part (CIP) application of a U.S. patent application Ser. No. 09/032,978, filed Mar. 2, 1998, now U.S. Pat. No. 6,290,666 which in turn is a divisional application of U.S. patent application Ser. No. 08/501,140, filed Aug. 15, 1995, now U.S. Pat. No. 5,766,209, which in turn is a National Stage application of PCT/FR/94/00171, filed Feb. 16, 1994, each incorporated herein by reference in its entirety.

BACKGROUND OF THE INVENTION

1. Field of Invention

The invention relates to methods and devices usable to place a stent in an anatomical constricting structure, such as, for example, a sphincter, using an easily-inserted and easily-withdrawn, self-stabilizing stent.

2. Description of Related Art

Prostheses usable to provide an artificial passage in anatomical tracts, such as, for example, the urinary, respiratory, digestive, gynecological or vascular tracts, in a living being are known. For example, an endo-urethral prosthesis for a human is known to have a tubular element whose walls are made from a relatively smooth and soft bio-compatible material, for example a silicone rubber, at least in its outer part. Such a tubular element is sufficiently flexible to conform to the anatomical profile and movements of, for example, a human urethra, while providing sufficient rigidity that the tubular element will not collapse under the influence of the anatomical profile or movements of the urethral tract.

As disclosed in FR-A-2 667 783, a tubular element, as described above, is placed in the urethra without passing through the striated muscles that form the sphincter in the urethral tract. The tubular element is supported primarily by the elasticity of the tubular element and the compressive force of the urethral wall. If the tubular element's diameter is large enough, the compressive forces of the elastic urethral wall may adequately secure the tubular element in the urethral tract. However, if the tubular element is too large, damage to the urethral wall may occur and withdrawal of the tubular element may be painful to the patient.

Alternatively, a smaller-diameter tubular element may be used, with notches formed in the outer wall of the tubular element, to provide a degree of secondary support for the tubular element within the urethral tract. However, such notches do not prevent the tubular element from moving downward, or descending, in the urethra during micturition, for instance. The changing position of the tubular element renders the tubular element problematic and risks discomfort to the patient. Further, providing the tubular element with scales, or fastening catches, to counter the tendency of the prosthesis to descend during micturition does not prevent the prosthesis from moving upward, or ascending, in the urethral tract as a result of routine bodily motions or functions. Such scales, or fastening elements also generate increased discomfort to the patient during withdrawal of the tubular element.

Other known catheter-delivered prostheses that provide an artificial passage in an anatomical tract of a living being include very flexible, spirally coiled metal elements. However, the flexible quality of the spirally coiled elements prove very unstable during insertion as the more rigid delivery catheter ends where the flexible element begins. As a result, bunching or other inappropriate placement of the flexible member often occurs, requiring withdrawal and re-insertion of the prosthesis, and/or causing discomfort to the patient due to the ill-configured element.

Still other known catheter-delivered prostheses that provide an artificial passage in an anatomical tract of a living being require ultra-sound, radioscopy, or other indirect visualizing devices to determine when and whether the prosthesis is in position to provide the artificial passage desired without inhibiting the natural constricting function of the anatomical constricting structure against the anatomical tract.

Thus, known tubular element prostheses are not self-stabilizing across a anatomical constricting structure. Nor are known prostheses provided with a method for inserting the prosthesis into and withdrawing the prosthesis from an anatomical tract that minimizes the pain and discomfort typically associated with stenting. Similarly, known prostheses do not have structures that provide a direct method for determining whether the catheter-delivered prosthesis is in the appropriate position in the anatomical tract such that the artificial passage is created without inhibiting the natural constricting function of the anatomical constricting structure against the anatomical tract.

SUMMARY OF THE INVENTION

This invention provides stent assemblies and methods usable to insert and withdraw a self-stabilizing prosthetic stent to or from an anatomical tract of a living being.

This invention separately provides stent assemblies and insertion/withdrawal methods that allow the self-stabilizing prosthetic stent to create an artificial passage within the tract in a manner that minimizes pain and discomfort to the living being.

This invention separately provides stent assemblies and insertion/withdrawal methods that enable a user to determine directly when the self-stabilizing prosthetic stent is properly placed.

In various exemplary embodiments, the self-stabilizing prosthetic stent comprises distal and proximal segments connected to one another via a flexible connection structure to form an approximately continuous outer surface of the self-stabilizing prosthetic stent. The approximately continuous outer surface of the self-stabilizing prosthetic stent permits non-traumatic insertion or withdrawal of the self-stabilizing prosthetic stent to or from an anatomical tract of a living being without needing anesthesia. In various exemplary embodiments, the distal and proximal segments are generally tubular elements that can be formed of a relatively smooth, soft bio-compatible material. This permits the distal and proximal segments to conform to the profile and movements of the anatomical tract that the self-stabilizing prosthetic stent is placed within. In various exemplary embodiments, each of the distal and proximal segments have a substantially constant cross-section.

In various exemplary embodiments, the self-stabilizing prosthetic stent's flexible connection structure includes a tubular, flexible sleeve having opposed first and second ends. The first end of the flexible connection structure connects to the self-stabilizing prosthetic stent's distal segment. The second end of the flexible connection structure connects to the self-stabilizing prosthetic stent's proximal segment. The flexible connection structure, when properly seated, lies adjacent to the anatomical constricting structure of the anatomical tract. The flexible quality of the flexible connection structure permits the natural function of the anatomical constricting structure to continue, thus creating the desired artificial passage in the anatomical tract.

In various exemplary embodiments, the stent assembly usable to insert and withdraw this self-stabilizing prosthetic stent structure includes one or more additional structural features permitting the insertion and withdrawal methods of the invention to be achieved.

In various exemplary embodiments, inserting the self-stabilizing prosthetic stent uses a delivery catheter, on which at least a portion of the self-stabilizing prosthetic stent is placed, to generally guide the self-stabilizing prosthetic stent into an anatomical tract. In various exemplary embodiments, the delivery catheter includes a semi-rigid, hollow mandrel usable to urge the distal stent segment into the anatomical tract, and a pusher to push the proximal stent segment, in a trailing fashion relative to the distal stent segment, to the desired position within the anatomical tract.

In these exemplary embodiments, the pusher is first placed upon the mandrel. The self-stabilizing prosthetic stent is then mounted upon the mandrel. The self-stabilizing prosthetic stent is then placed into the anatomical tract such that a generally closed end of the distal stent segment enters the anatomical tract first. The flexible connection structure joins the distal stent segment to the proximal stent segment and also is mounted upon the mandrel. Mounting the self-stabilizing prosthetic stent in this manner upon the mandrel precludes the flexible connection structure from deforming until after the mandrel is withdrawn. The hollow mandrel is provided with an opening on one end that aligns with a similar opening in the closed, rounded end of the distal stent segment. Aligning the openings in the mandrel and the distal stent segment permits fluid to flow into and through the self-stabilizing prosthetic stent and mandrel.

Together, the mandrel and the pusher advance and maintain the self-stabilizing prosthetic stent, particularly the distal stent segment, into a desired position relative to a target organ and/or body cavity as the stent assembly delivers the self-stabilizing prosthetic stent into and through the anatomical tract, and ultimately to the target organ and/or body cavity. An end of the proximal segment of the self-stabilizing stent, furthest from the flexible connection structure, is provided with an eyelet from which one or more withdrawal threads, pull-wires, or equivalent structures extend outwardly through the anatomical tract to be accessible outside of the living being.

Combined with the delivery catheter, the self-stabilizing prosthetic stent is inserted to the desired anatomical tract until the proximal and distal segments of the self-stabilizing prosthetic stent extend at least partly across an anatomical constricting structure and until the closed end of the distal segment reaches a desired position relative to the target body cavity or organ, such as, for example, extending into a bladder. The openings in the distal segment's closed end and in the mandrel are aligned such that a flow of fluid through the self-stabilizing prosthetic stent and in the mandrel occurs, signaling that the self-stabilizing prosthetic stent has reached a desired location relative to the target organ and/or body cavity. Thus, general placement of the self-stabilizing prosthetic stent is achieved without needing ultrasound, radioscopy, or other visualizing methods or devices.

The mandrel is then withdrawn, while the pusher is maintained in place. Once the mandrel is withdrawn, the flexible connection structure is available and will flex in response to the natural constricting or relaxing functions of the anatomical constricting structure. Then, the pusher is withdrawn. The one or more withdrawal threads, pull-wires, or other equivalent structures that extend from the self-stabilizing prosthetic stent is accessible outside of the living being. At least one of the withdrawal threads, pull-wires, or other equivalent structures is then gently tugged until the flexible connection structure of the self-stabilizing prosthetic stent is fully extended and seated within the anatomical constricting structure.

Thus, specific placement of the self-stabilizing prosthetic stent and the flexible connection structure is easily identified as increased resistance to tugging on the at least one withdrawal thread, pull-wire, or other equivalent structure is sensed when the flexible connection structure is seated in the anatomical constricting structure. Further, the natural function of the anatomical constricting structure causes the flexible connection structure to close, thus stopping the flow of fluid through the self-stabilizing prosthetic stent and directly indicating that the self-stabilizing prosthetic stent is appropriately positioned within the anatomical tract. Accordingly, an artificial passage, complying with the natural functions and configurements of the anatomical tract, is achieved.

Withdrawing the self-stabilizing prosthetic stent is accomplished by providing a more constant pulling on at least one of the withdrawal threads, pull-wires, or other equivalent structures of the self-stabilizing prosthetic stent so that the constricting forces of the anatomical constricting structure are overcome. Having overcome the anatomical constricting forces, the self-stabilizing prosthetic stent can be freely removed from the anatomical tract with reduced pain or discomfort.

In other exemplary embodiments of the stent assembly and insertion and withdrawal methods of this invention, the self-stabilizing prosthetic stent is mounted upon a delivery catheter. In various exemplary embodiments, the proximal and distal stent segments abut one another during insertion due to the flexible connection structure joining the distal and proximal stent segments being in a collapsed state. An end of a distal stent segment release structure protrudes through a wall of the delivery catheter to hold the distal stent segment in place during insertion. The distal stent segment has a generally closed end that is placed relative to a target organ and/or cavity, and an opening through which fluid flows when the self-stabilizing prosthetic stent reaches the target organ or body cavity. A stiff member is used during insertion of the self-stabilizing prosthetic stent to position the distal segment of the self-stabilizing prosthetic stent, or to more securely maintain the position of the distal segment in the anatomical tract and relative to the target organ and/or body cavity.

An end of a proximal stent segment release structure protrudes through the wall of the delivery catheter to hold the proximal stent segment in place during insertion, such that the proximal and distal stent segments are maintained in an abutting relationship during insertion until the respective release structures are withdrawn. Fluid flow through the opening in the generally closed end of the distal stent segment signals that the self-stabilizing prosthetic stent has reached the target organ and/or body cavity. The distal stent segment release structure, the proximal stent segment release structure, and the delivery catheter are removed in any one of a number of different orders, depending on which exemplary embodiment is being used, to seat the flexible connection structure of the self-stabilizing prosthetic stent in the anatomical constricting structure.

Proper positioning of the flexible connection structure is easily detected as the fluid flow from the target organ through the self-stabilizing prosthetic stent and the delivery catheter ceases as the flexible connection structure extends such that the proximal and distal stent segments no longer abut one another. By seating the flexible connection structure of the stent in the region of the anatomical constricting structure, the natural functioning of the anatomical constricting structure is permitted and the desired artificial passage in the anatomical tract is achieved.

In still other various exemplary embodiments, the proximal and distal stent segments, in a non-abutting relationship to one another, are mounted upon a hollow delivery catheter such that the flexible connecting structure joining the proximal and distal stent segments is substantially extended during insertion of the stent to the anatomical tract. Fluid flow through the hollow delivery catheter and stent again indicates the stent has reached the target organ and/or body cavity. Withdrawal of the delivery catheter permits the natural constricting and relaxing functions of the anatomical constricting structure to act upon the flexible connecting structure of the stent. Again, gentle tugging on at least one of the one or more withdrawal threads, pull-wires, or other equivalent structures enables the flexible connecting structure to be seated more compliantly with the anatomical constricting structure desired.

Withdrawing the self-stabilizing prosthetic stent is accomplished by providing a more constant pulling on at least one of the one or more withdrawal threads, pull-wires, or other equivalent structures so that the constricting forces of the anatomical constricting structure are overcome. Having overcome the anatomical constricting forces, the self-stabilizing prosthetic stent is freely removable from the anatomical tract.

It should be appreciated that in all of the exemplary embodiments the self-stabilizing prosthetic stent may also be used to instill fluids, or other irrigating solutions, to the target organ and/or body cavity. Further, the stent assemblies and stent insertion and withdrawal methods according to this invention may be used to insert or control other instruments, such as, for example, an endoscope, to view or otherwise involve a target body cavity or organ by deploying an instrument through the stent assembly and self-stabilizing prosthetic stent using the methods described.

It should be further appreciated that, in all of the exemplary embodiments, the flexible connecting structure may be tubular, threaded, slotted, or any equivalent structural combination permitting the seating of the flexible connecting structure for compliance with the naturally occurring actions within the anatomical constricting structure the flexible connecting structure is subject to, such as, for example, the structures disclosed in the incorporated U.S. Pat. No. 5,766,209.

It should be still further appreciated that the terms "distal" and "proximal" as used herein are exemplary only with reference to the insertion entry point of the self-stabilizing prosthetic stent after the self-stabilizing prosthetic stent is inserted into the anatomical tract.

The simplicity of the insertion and withdrawal methods and structures according to this invention permit non-specialists to place successfully a stent in a living being relatively painlessly, and without needing anesthesia. Further, appropriately positioning the self-stabilizing prosthetic stent can be achieved without expensive visualizing equipment, because the appropriate placement of the self-stabilizing prosthetic stent across the anatomical constricting structure is determined directly based on the flow of fluid or gases through the self-stabilizing prosthetic stent, by feeling the resistance to further withdrawal of the stent, and/or by the living being controlling, for example, micturition by voluntarily controlling, for example, the sphincter across which the flexible connecting structure of the self-stabilizing stent is placed.

These and other features and advantages of this invention are described in, or are apparent from, the detailed description of various exemplary embodiments of the systems and methods according to this invention.

BRIEF DESCRIPTION OF THE DRAWINGS

Various exemplary embodiments of this invention will be described in detail with reference to the following figures, wherein like numerals represent like elements, and wherein:

FIG. 6 illustrates a first exemplary embodiment of a stent assembly according to this invention;

FIG. 7 illustrates the exemplary embodiment shown in FIG. 6 in an assembled state;

DETAILED DESCRIPTION OF PREFERRED EMBODIMENTS

Figure 1:
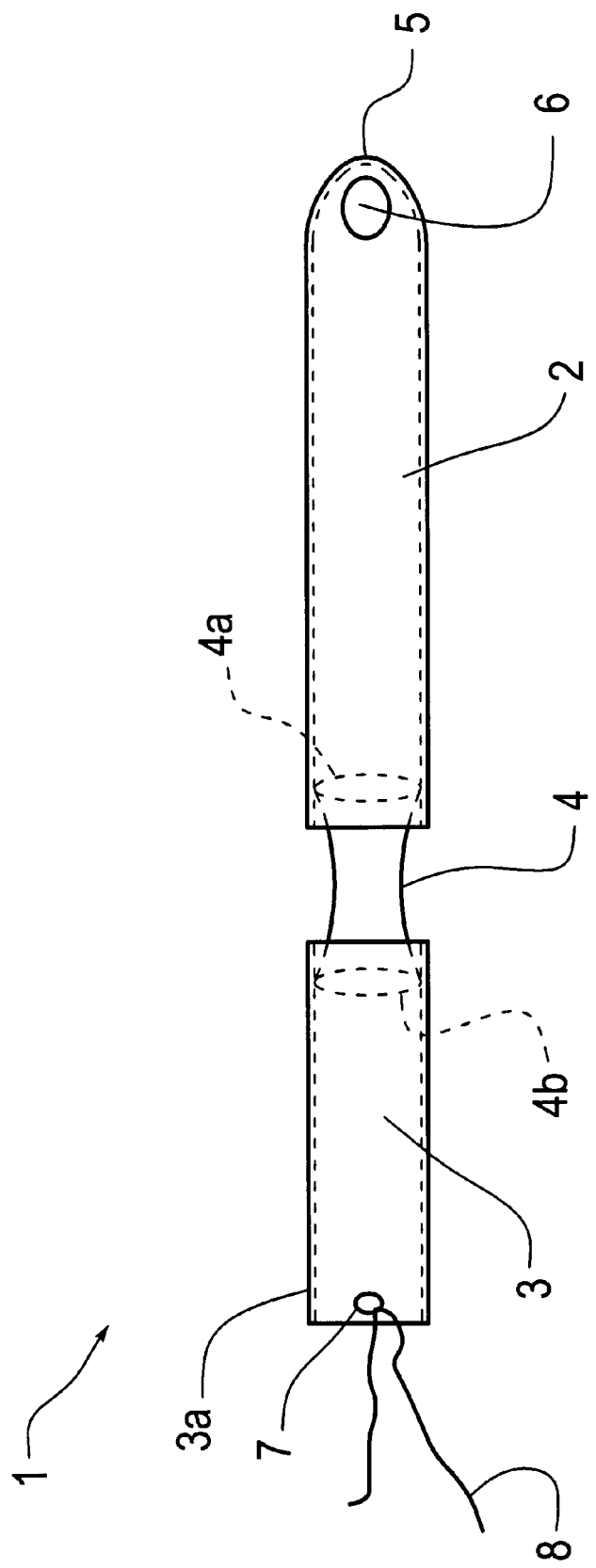
FIG. 1 illustrates a first exemplary embodiment of the general configuration of the self-stabilizing prosthetic stent according to this invention.

FIG. 1 shows a first exemplary embodiment of a self-stabilizing prosthetic stent 1. As shown in FIG. 1, the stent 1 includes a distal segment 2, a proximal segment 3 and a flexible connection structure 4. In various exemplary embodiments, the distal segment 2 and proximal segment 3 are tubular elements. In some exemplary embodiments, one or both of the distal segment 2 and/or the proximal segment 3 have substantially constant cross-sections. In various exemplary embodiments, the distal and proximal segments 2 and 3 are made of bio-compatible materials, such as silicone rubber, to provide a sufficiently flexible stent 1. However, the distal and proximal segments 2 and 3 can be made of any suitable material that is conformable to the profile and movements of the anatomical tract that the stent 1 is placed within, while maintaining a rigidity sufficient to create an artificial passage within that anatomical tract. In various exemplary embodiments, at least an outer surface of the stent 1 is made of a smooth material, such as, for example, silicone rubber. When smooth, the outer surface of the stent 1 provides for a more non-traumatic insertion or withdrawal of the stent 1 from the anatomical tract.

In various exemplary embodiments, the flexible connection structure 4, as shown in FIG. 1, is a soft, flexible sleeve. In general, the connection structure 4 will have a flexibility that is greater than the flexibility of the distal or proximal segments 2 and 3. Additionally, in various exemplary embodiments, either or both of the walls comprising the connection structure 4 can be thinner than the walls comprising the distal or proximal segments 2 and 3. This contributes to the relatively greater flexibility of the connection structure 4. The connection structure 4 has two opposed ends 4a and 4b. The first end 4a of the connection structure 4 is connected to the interior surface of the distal segment 2. The second end 4b of the connection structure 4 is similarly connected to the interior surface of the proximal segment 3. This provides continuity between the distal and proximal segments 2 and 3. By connecting the distal and proximal segments 2 and 3 using the flexible connection structure 4, the stent 1 has an approximately continuous outer surface.

Figure 2:
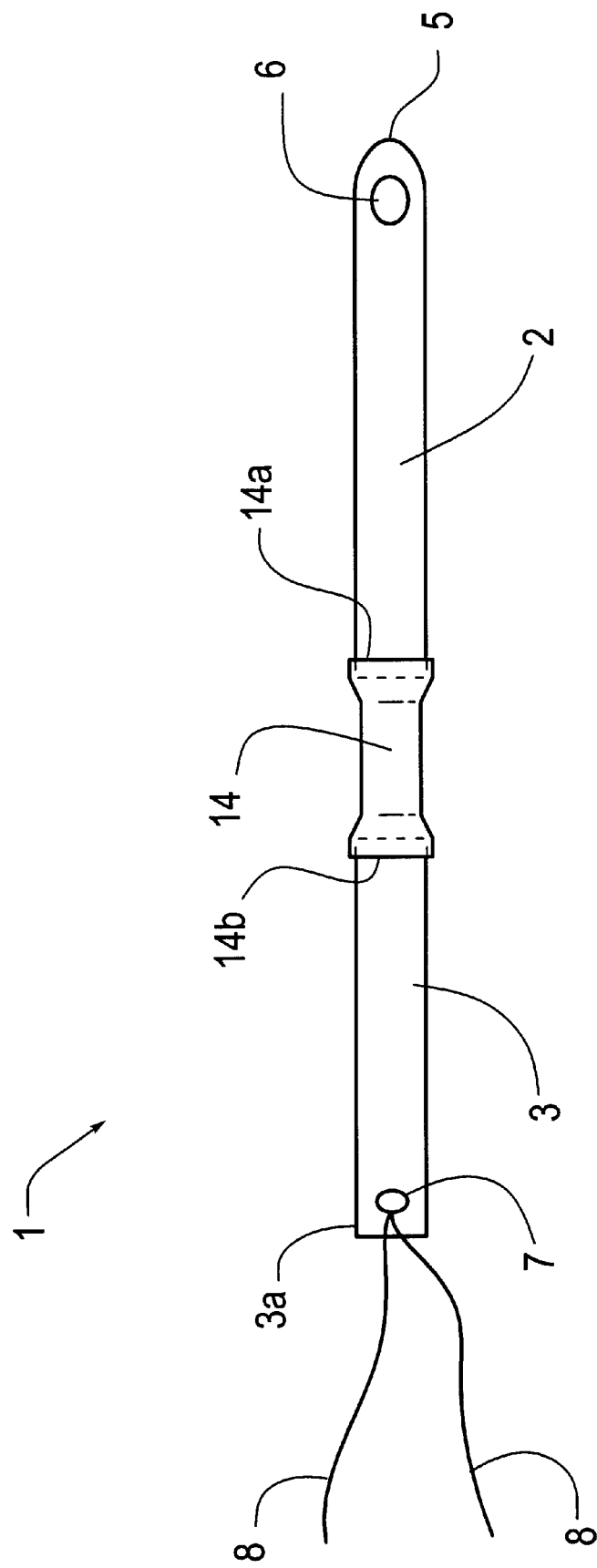
FIG. 2 illustrates a second exemplary embodiment of the general configuration of the self-stabilizing prosthetic stent according to this invention.

FIG. 2 shows a second exemplary embodiment of the stent 1. As shown in FIG. 2, the second exemplary embodiment of the stent 1 includes a flexible connection structure 14 having two opposed ends 14a and 14b connected to the distal and proximal segments 2 and 3, respectively. The flexible connection structure 14 of the second exemplary embodiment of the stent 1 can be generally similar to the structures and/or materials of the flexible connection structure 4 of the first exemplary embodiment of the stent 1. However, as shown in FIG. 2, the flexible connection structure 14 is connected to the outer surface of the distal and proximal segments 2 and 3 using the first end 14b and the second end 14b. The flexible connection structures 4 and 14 may be attached to the distal and proximal segments 2 and 3 in any suitable manner, such as, for example, by adhesive bonding. Thus, it should be appreciated that any known or later developed suitable attachment structures and methods could be used.

The flexible connection structures 4 and 14 thus provide a predetermined region that complies with and permits the continuation of the natural functioning of an anatomical constricting structure, such as, for example, a sphincter, when the stent 1 is placed within the anatomical tract to create an artificial passage. The flexible connection structures 4 and 14 each further provides a self-stabilizing quality to the stent 1 when the stent 1 is inserted into the anatomical tract. That is, when the flexible connection structure 4 or 14 is positioned in alignment with the anatomical constricting structure, such as the sphincter, of the anatomical tract, the location of the stent 1 in the anatomical tract is stable. That is, the stent 1 does not readily move within the anatomical tract.

The distal segment 2, at the end opposite the connection structure 4 or 14, includes a generally closed end 5. The closed, rounded end 5 serves as an entry end of the distal stent segment 2 of the stent 1. The generally closed end 5 promotes the non-traumatic insertion of the stent 1 into the anatomical tract. The generally closed end 5 of the stent 1 further includes at least one orifice or opening 6 that permits fluid to flow into and through the stent 1. As shown in FIGS. 1 and 2, in various exemplary embodiments, the at least one orifice or opening 6 is a lateral orifice or opening 6 that opens in the side wall of the distal segment 2 of the stent 1. In this case, the generally closed end 5 is a completely closed end 5. In general, in various exemplary embodiments, when the generally closed end 5 is completely closed, the generally closed end 5 can be rounded.

In various other exemplary embodiments of the distal segment 2, the at least one orifice or opening 6 can be formed in the end wall of the generally closed end 5. That is, the distal segment 2 forms a tube have two open ends. In this case, the generally closed end 5 is not completely closed. However, in various exemplary embodiments, the generally closed end 5 can be narrowed relative to the diameter of the rest of the distal segment 2. This will allow a mandrill, such as that shown in FIG. 6, or a stiff member, such as that shown in FIG. 13, to be placed into the distal segment 2 of the stent 1 to aid in advancing the stent 1 into the anatomical traps. In still other exemplary embodiments, the generally closed end 5 can be completely open, such that the closed end 5 is not closed at all. In this case, one or more constricting structures can be placed within the distal segment 2 to provide surfaces against which the mandrill shown in FIG. 6 or the stiff member shown in FIG. 13 can bear against to advance the distal segment 2 into the anatomical tract.

The proximal segment 3 of the stent 1 includes an eyelet hole 7. The eyelet hole 7 is formed in an end 3a of the proximal segment 3 furthest from the connection structure 4 or 14. The one or more withdrawal threads, pull-wires, or other equivalent structures 8 extend from the eyelet hole 7. The one or more withdrawal threads, pull-wires, or other equivalent structures 8 are accessible to a user outside the anatomical tract, even after the stent 1 has been inserted into the desired anatomical tract. The one or more withdrawal threads, pull-wire, or other equivalent structures 8 enable a user to pull on at least one of the withdrawal threads, pull-wires, or other equivalent structures 8 to position the stent 1 more precisely within the anatomical constricting structure region, and/or to remove the stent 1 from the anatomical tract in a relatively smooth and painless manner.

Figure 3:
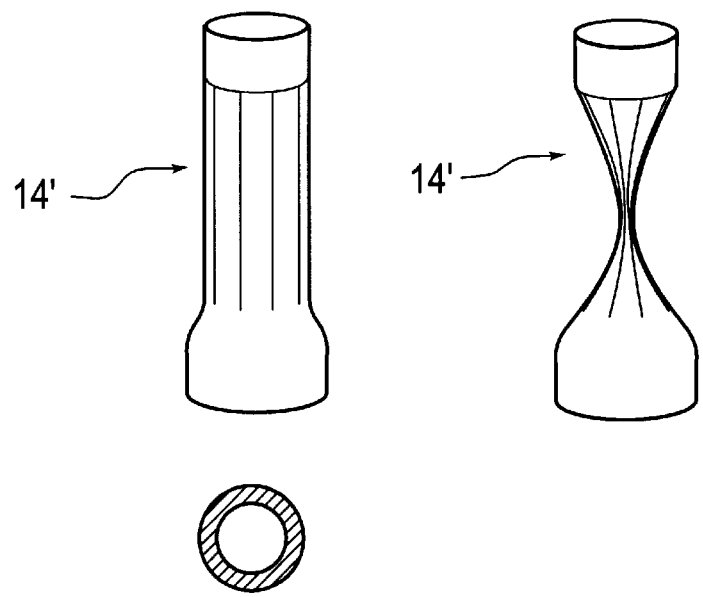
FIG. 3 illustrates an exemplary embodiment of a perforated flexible connection structure according to this invention.
Figure 4:
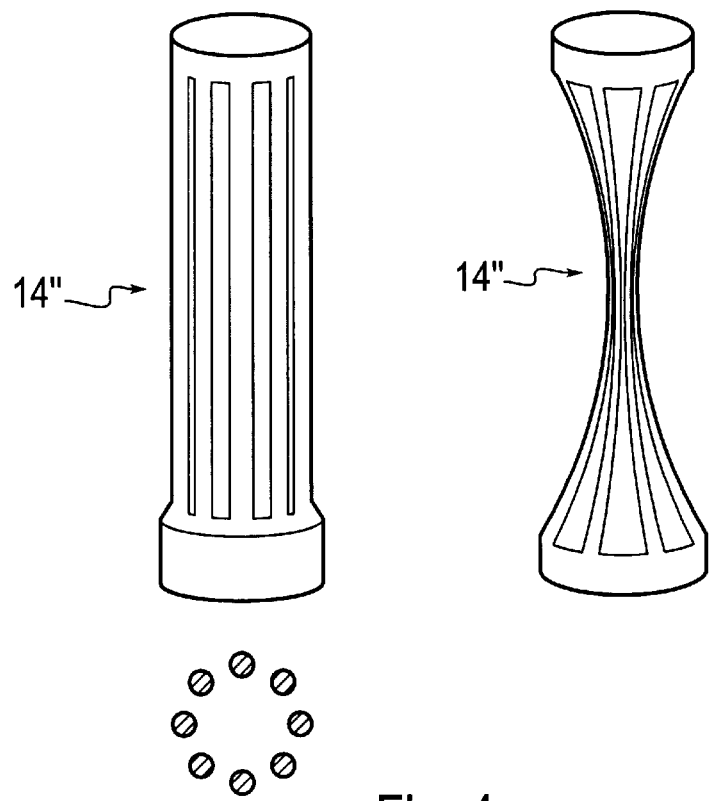
FIG. 4 illustrates an exemplary embodiment of a slotted flexible connection structure according to this invention.

FIGS. 3 and 4 show third and fourth exemplary embodiments of the flexible connection structure 14' and 14". While the first and second exemplary embodiments of the flexible connection structures 4 or 14 described above are tubular elements having generally solid sides, as shown in FIGS. 1 and 2, it should be appreciated that the flexible connection structure of the stent 1 may instead have perforated sides, as in the flexible connection structure 14' shown in FIG. 3. Alternatively, the flexible connection structure may have slotted sides, as in the flexible connection structure 14" shown in FIG. 4. The perforations or slots in the flexible connection structures 14' and 14", respectively, render it easier to bend or otherwise deform the flexible connection structures 14' and 14", thus contributing to voluntary control by the patient of the functioning of the anatomical constricting structure.

Figure 5:
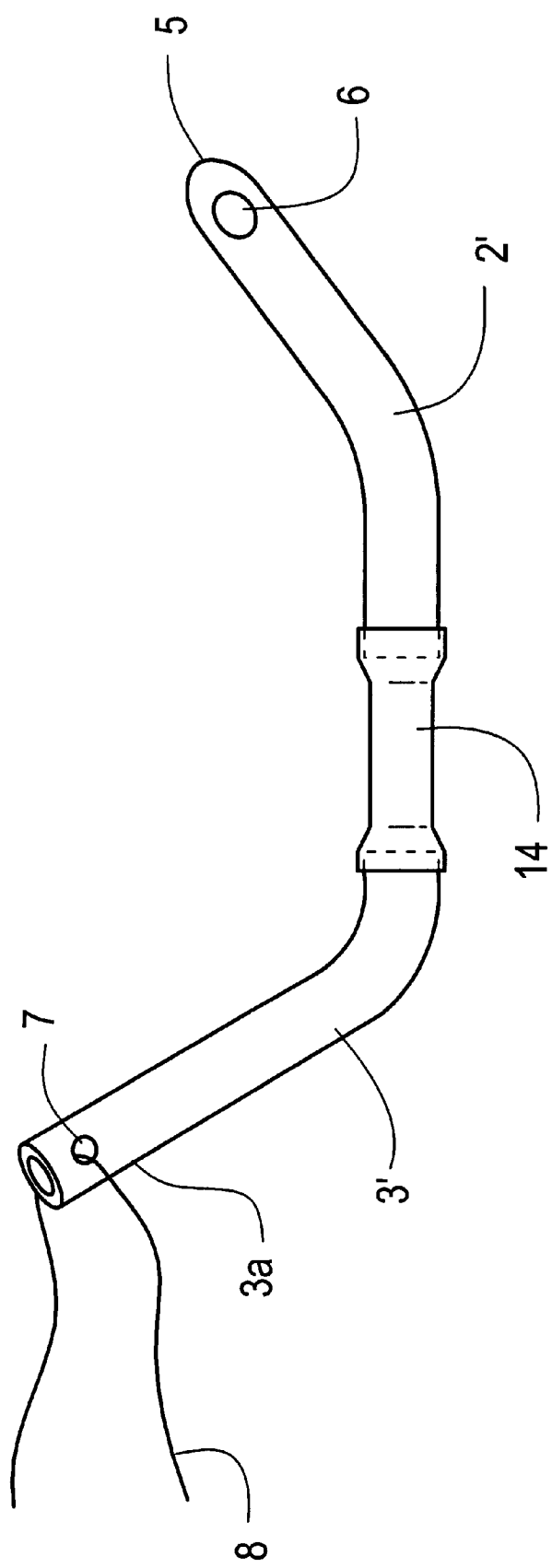
FIG. 5 illustrates various exemplary embodiments of angularly adapted stent segments according to this invention.
Figure 8:
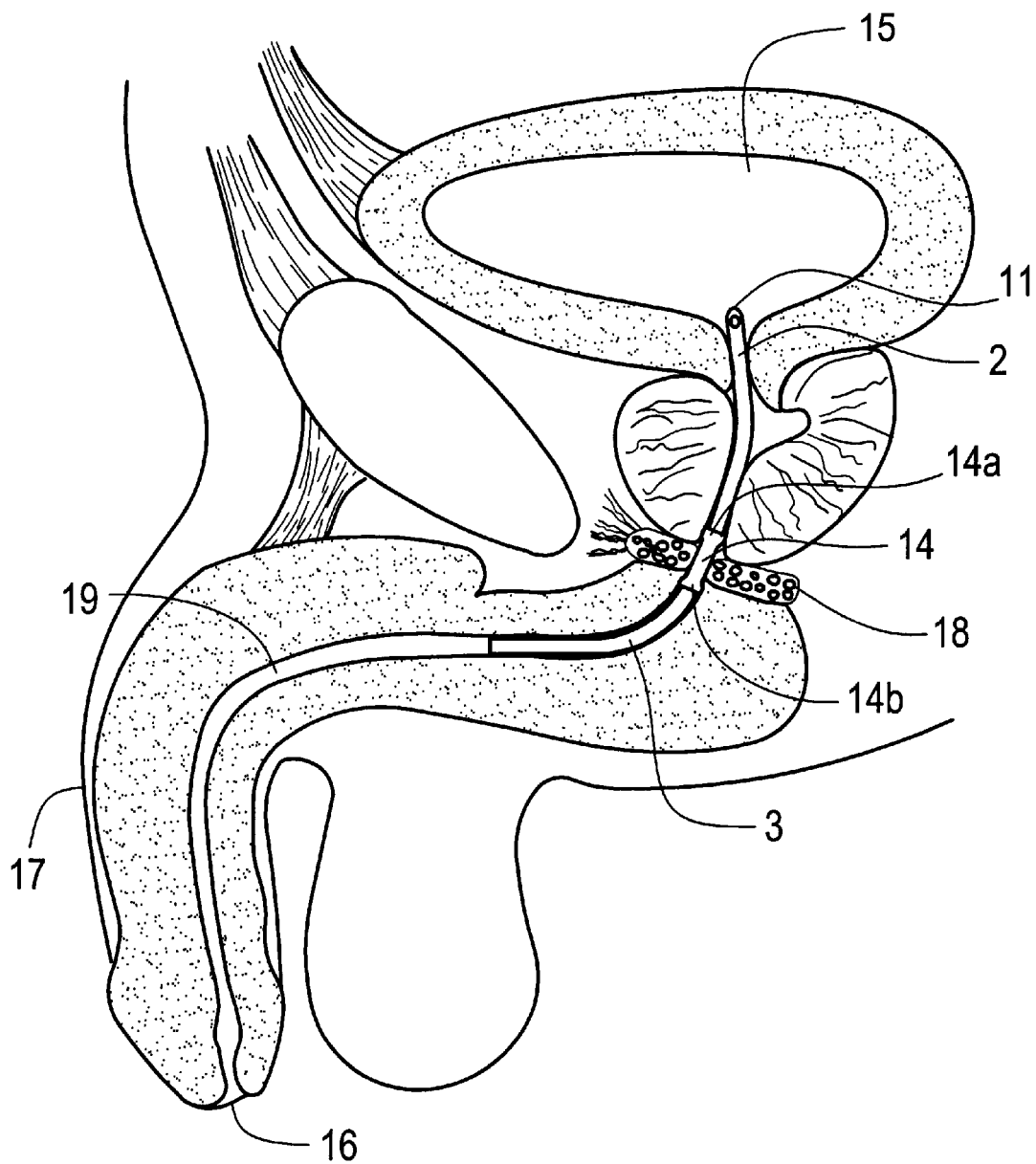
FIG. 8 illustrates an example of the self-stabilizing prosthetic stent located across a sphincter of a male urethra after insertion of the self-stabilizing prosthetic stent according to this invention.
Figure 9:
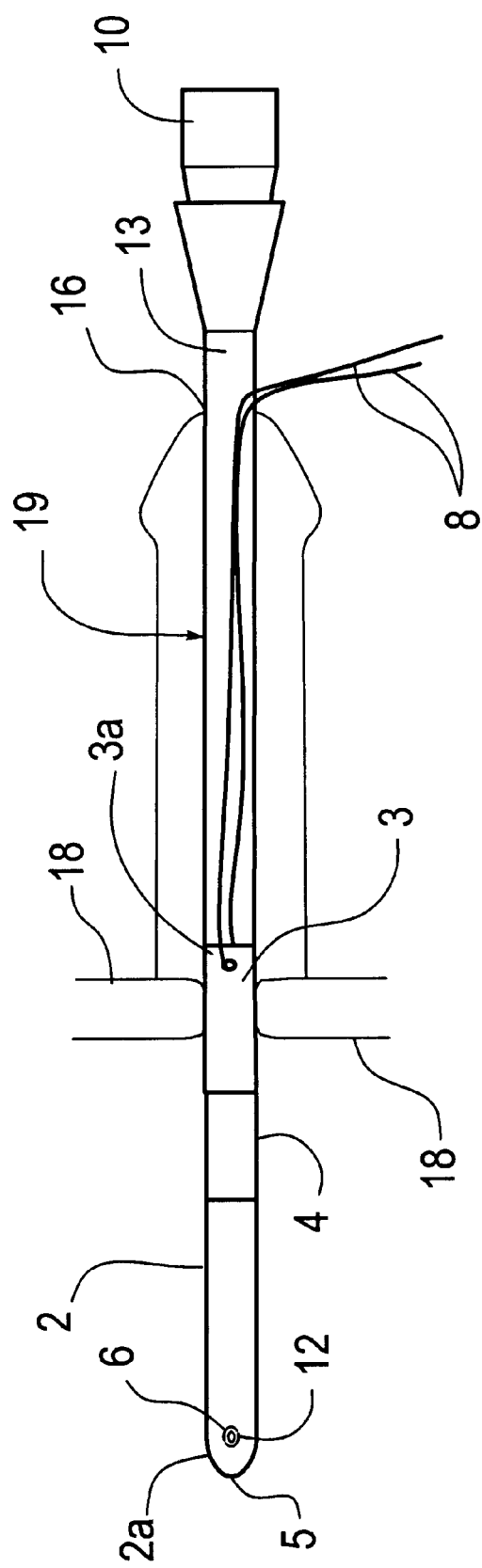
FIGS. 9–12 illustrate a first exemplary embodiment of a method for positioning of the self-stabilizing prosthetic stent within a human male's penis for insertion of the self-stabilizing prosthetic stent according to this invention using the stent assembly of FIGS. 6 and 7.
Figure 10:
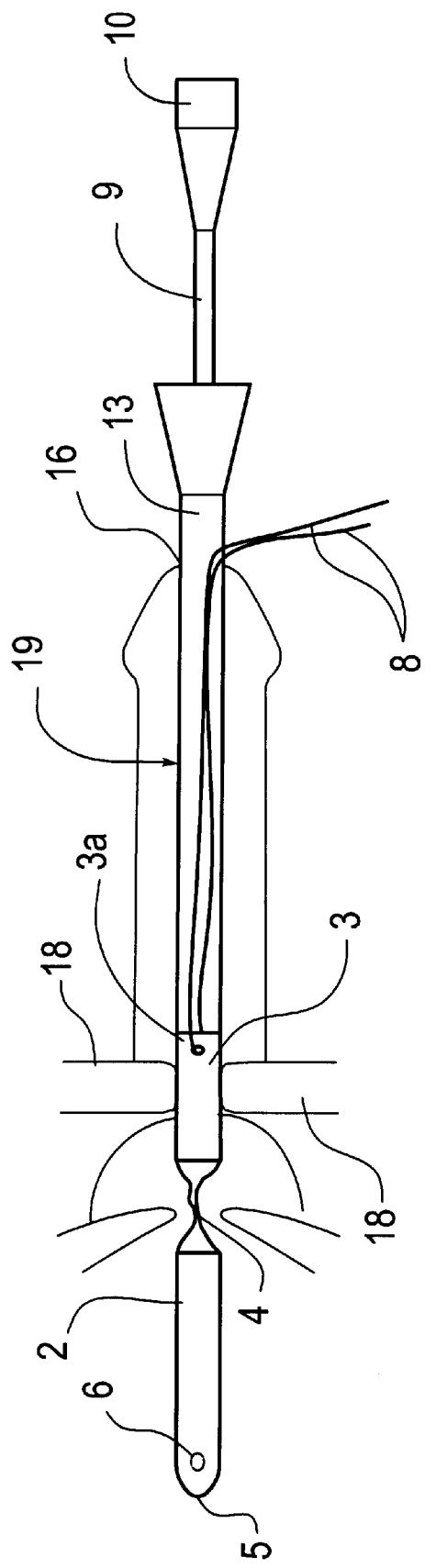
Figure 11:
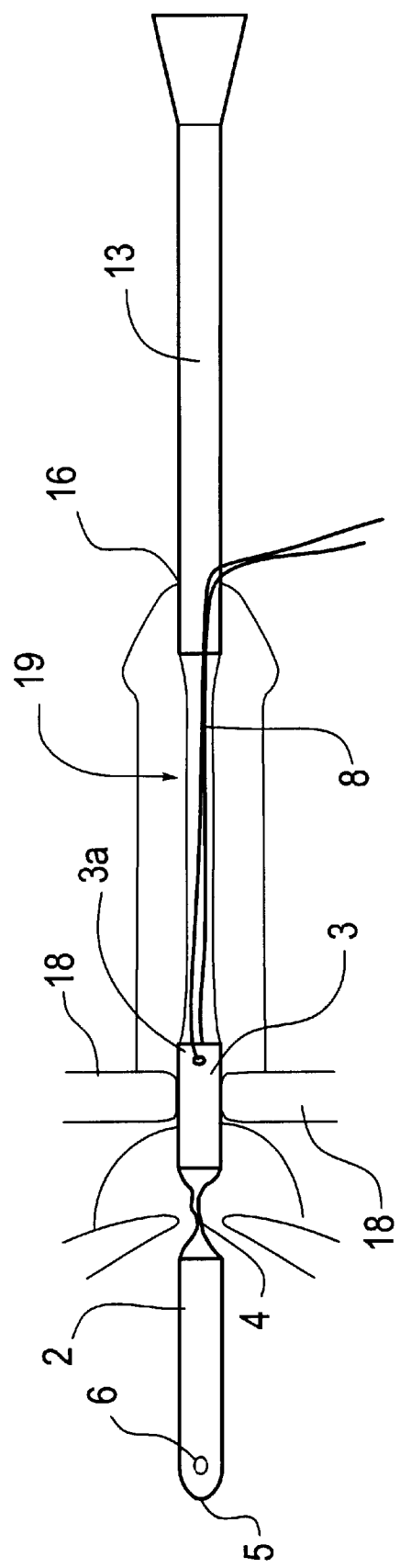
Figure 12:
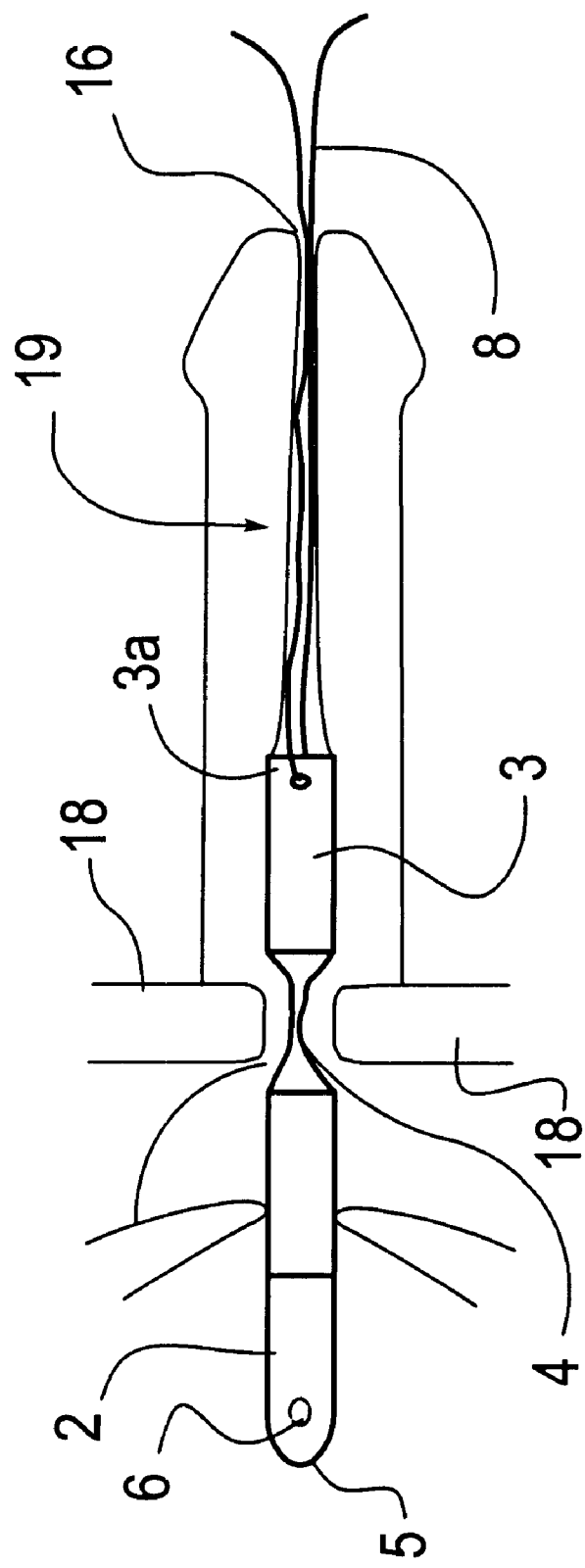

While FIGS. 1 and 2 show the distal and proximal segments 2 and 3 as essentially linear, as in FIGS. 1 and 2, it should be appreciated that one or both of the distal and/or proximal segments 2 and 3 may be angularly adapted to conform to the profile of the portion of the anatomical tract that the distal and proximal segments 2 or 3 will be inserted into. FIG. 5 shows one exemplary embodiment of a stent 1 having an angularly adapted distal segment 2', and an angularly adapted proximal segment 3'. The angularly adapted distal or proximal segments 2' and 3' may be identical to or different from the natural angulation of the anatomical tract the stent 1 is to be placed into. The angularly adapted distal and/or proximal segments 2' and/or 3' may ease insertion or withdrawal of the stent 1, and/or may help secure the stent 1 in a desired position once placed within the anatomical tract.

FIGS. 6 and 7 show a first exemplary embodiment of a stent assembly 100 that includes the various components outlined above, assembled for inserting the stent 1 into, or withdrawing the stent 1 from a living being according to the methods of this invention. The stent assembly 100 includes a hollow mandrel 9 having an external cross-section that is adapted to receive the stent 1, including one of the flexible connection structures 4 or 14. In various exemplary embodiments, the mandrel 9 is formed of a semi-rigid material. The mandrel 9 has an end-stop 10 and a generally closed end 11. The generally closed end 5 of the distal segment 2 of the stent 1 abuts the generally closed end 11 of the mandrel 9 when the stent 1 is mounted on the mandrel 9 for insertion to an anatomical tract. An eyelet 12 is formed in the generally closed end 11 of the mandrel 9. The eyelet 12 can be aligned to match the orifice or opening 6 of the distal segment 2 when the stent 1 is engaged with the mandrel 9. Thus, the generally closed end 11 can have any of the structures described above for the generally closed end 5. By aligning the eyelet 12 and orifice or opening 6, fluid can flow from a body cavity or organ, such as, for example, a bladder, once the stent 1 has been inserted through the anatomical tract far enough to penetrate, for example, the bladder.

A hollow pusher 13 has an internal cross-section that allows the pusher 13 to be placed or mounted on the mandrel 9. The pusher 13 spaces the proximal segment 3 of the stent 1 from the end-stop 10 of the mandrel 9 when the stent 1 is mounted on the mandrel 9 for insertion into the anatomical tract. In various exemplary embodiments, the hollow pusher 13 is formed of a rigid material.

The stent 1, including its proximal and distal segments 2 and 3 and one of the flexible connection structures 4 or 14, along with the mandrel 9 and the pusher 13, forms the stent assembly 100 for inserting the stent 1 into an anatomical tract. FIG. 7 shows the various elements of the stent assembly 100 assembled into a single assembly for inserting the stent 1 into an anatomical tract. As shown in FIG. 7, the end 3a of the proximal stent segment 3 abuts the pusher 13. The pusher 13 is mounted on the mandrel 9 and spaces the proximal segment 3 of the stent 1a distance L from the end-stop 10 of the mandrel 9. At the same time the generally closed end 5 of the distal stent segment 2 of the stent 1, when mounted on the mandrel 9, abuts the generally closed end 11 of the mandrel 9. The stent 1 is aligned so that the orifice or opening 6 of the distal segment 2 is adjacent to the eyelet 12 of the mandrel 9. The one of the flexible connection structures 4 or 14 can be relaxed or can be fully extended as that flexible connection structure 4 or 14 joins the distal and proximal segments 2 and 3. However, the position of that flexible connection structure 4 or 14 on the mandrel 9 precludes that flexible connection structure 4 or 14 from bending or complying with the natural constricting function of the anatomical constricting structure, such as, for example, a sphincter, until the mandrel 9 is withdrawn at least from within that flexible connecting structure 4 or 14. The anatomical tract into which the stent 1 will be placed may be lubricated to ease the insertion or subsequent withdrawal process.

By way of example only, as shown for example in FIGS. 8 to 12, once assembled, the stent assembly 100 can be inserted to the urethral tract 19 of a human male through the urethral meatus 16 of the penis 17 until the generally closed end 5 of the distal segment 2 and the generally closed end 11 of the mandrel 9 enters into the bladder 15. Insertion of the stent 1 and mandrel 9 into the urethral tract 19 is eased by positioning the penis 17 in a direction compliant with the linearly projecting mandrel 9, as shown, for example, in FIG. 9. Because the orifice or opening 6 of the distal segment 2 and the eyelet 12 of the mandrel are aligned, urine flows through the orifice or opening 6 and eyelet 12 and into the mandrel 9 once the stent 1 is placed into the bladder 15. The fluid flow through the mandrel 9 indicates directly, without radioscopy or other indirect visualizing means, that the stent 1 has reached its target organ, which is, in this instance, the bladder 15.

Thus far in this exemplary insertion process, the stent 1 maintains its approximately continuous outer surface such that the mandrel-mounted stent 1, and the flexible connection structure 4 or 14 in particular, bridges the anatomical constricting structure, such as, for example, the sphincter 18, prohibiting the sphincter 18 from closing. Thereafter, the mandrel 9 is withdrawn, although the pusher 13 is maintained in place abutting the proximal segment 3. As a result, the stent 1 does not drift or move from its position bridging the sphincter 18 and penetrating into the bladder 15.

Next, the pusher 13 is removed. If the flexible connection structure 4 or 14 has been properly seated into the desired location within the sphincter 18, a gentle tug on at least one of the withdrawal threads, pull-wires, or other equivalent structures 8 may be used to move the flexible connection structure 4 or 14 until that flexible connecting structure 4 or 14 is appropriately seated relative to the sphincter 18 region.

The desired position of the stent 1 is thus easily determined by the user inserting the stent 1, since the sphincter 18 closes on the flexible connection structure 4 or 14 providing a resistance to further tugging on at least one of the withdrawal threads, pull-wires, or other equivalent structures 8. Further, once the sphincter 18 closes, the flow of fluid from the bladder 15 stops. Thus, the appropriate positioning of the stent is easily achieved, without expensive visualization tools or devices.

Withdrawing the stent 1 from the anatomical tract 19 according to the first exemplary embodiment of the method for inserting and withdrawing the stent 1 is accomplished by pulling steadily on at least one of the withdrawal threads, pull-wires, or other equivalent structures 8 with a force sufficient to overcome the resistance of the anatomically constricting structure, such as, for example, the muscles of the sphincter 18. This force releases the flexible connection structure 4 or 14 from the region of the anatomical constricting structure, such as, for example, the region adjacent to the sphincter 18. Once released from the region of the anatomical constricting structure, such as the region adjacent to the sphincter 18, the stent 1 descends through the anatomical tract 19 until the stent 1 is completely withdrawn from the anatomical tract 19.

Figure 13:
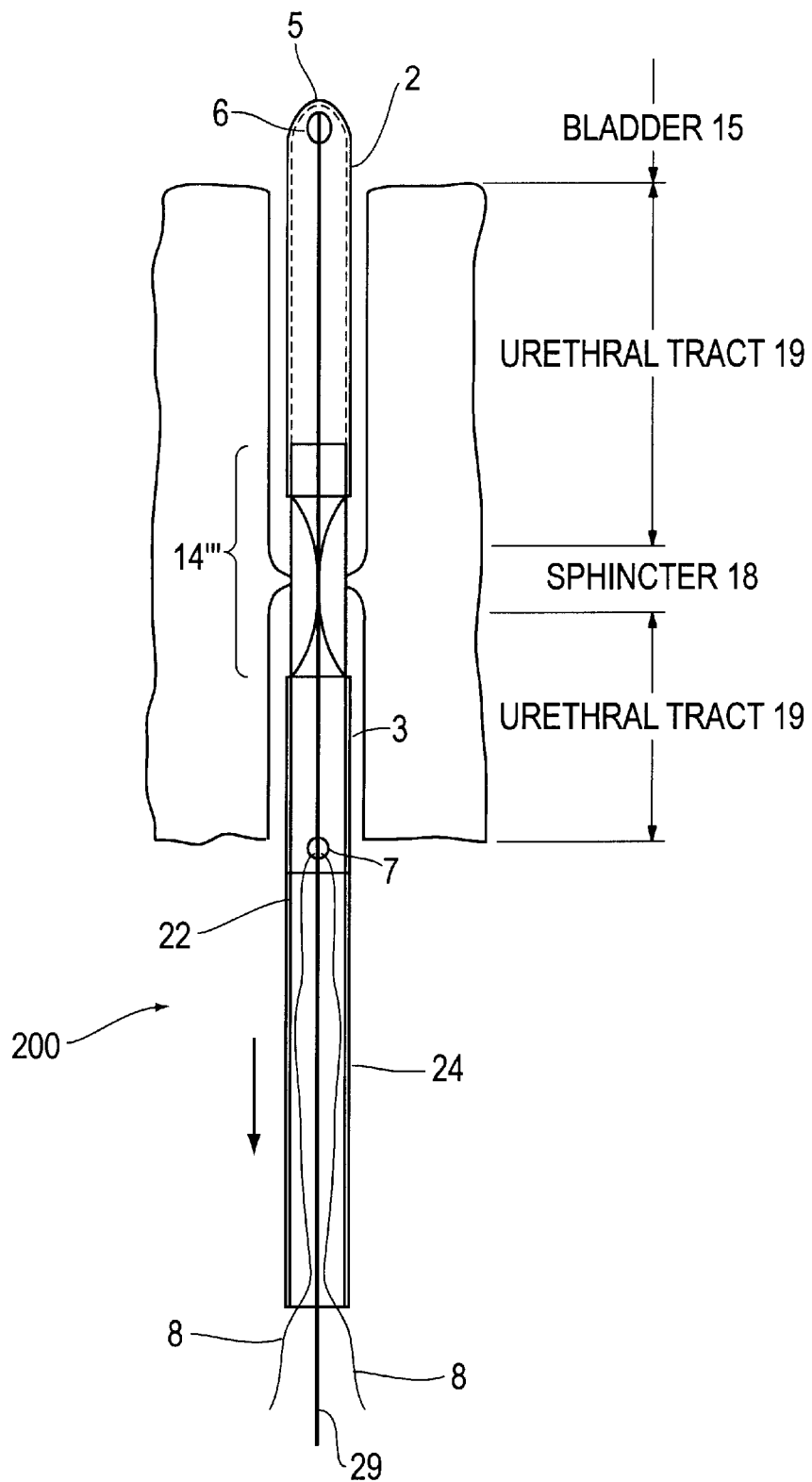
FIGS. 13–15 illustrate a second embodiment of a method for inserting the self-stabilizing prosthetic stent according to this invention using a second exemplary embodiment of the stent assembly.
Figure 14:
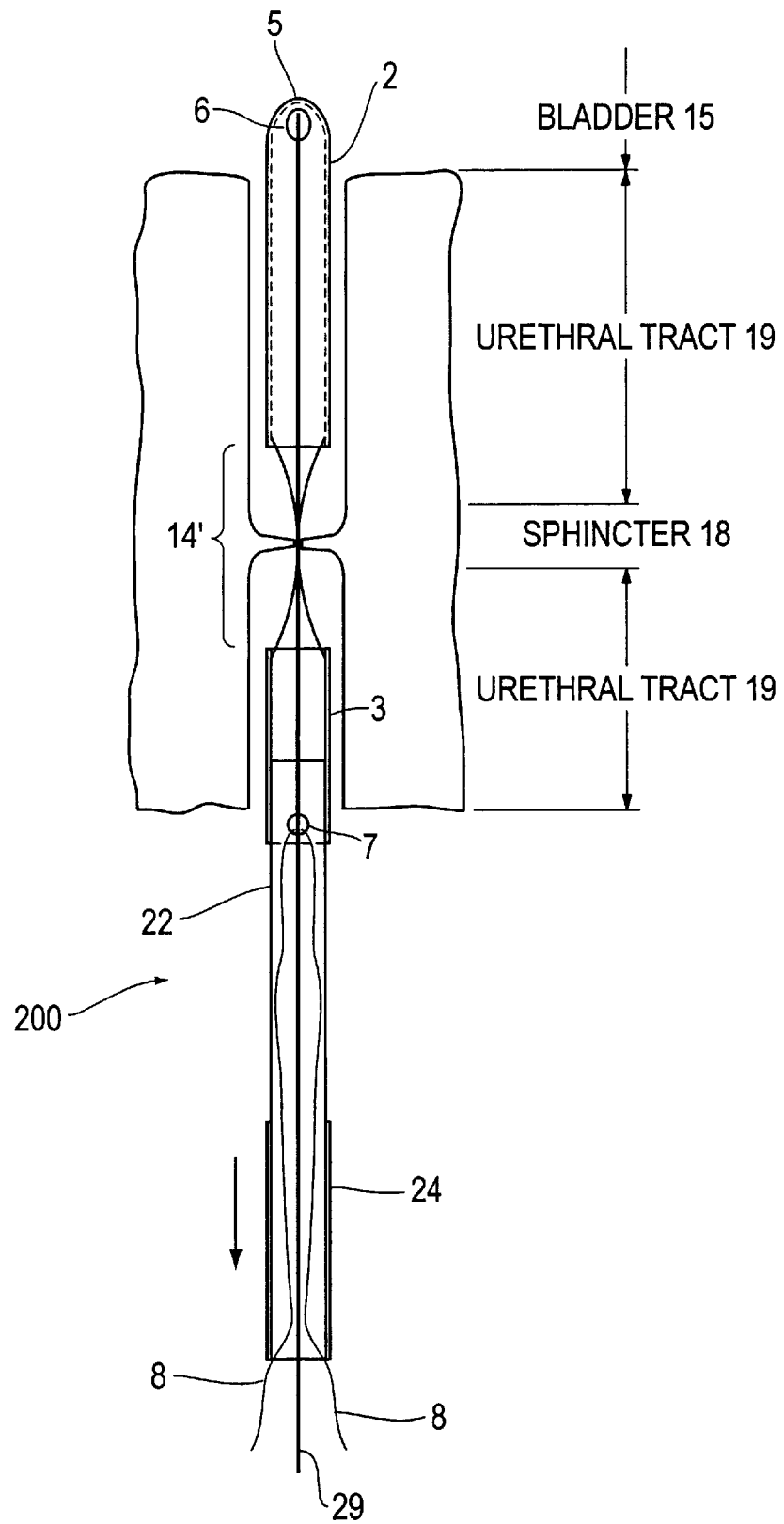
Figure 15:
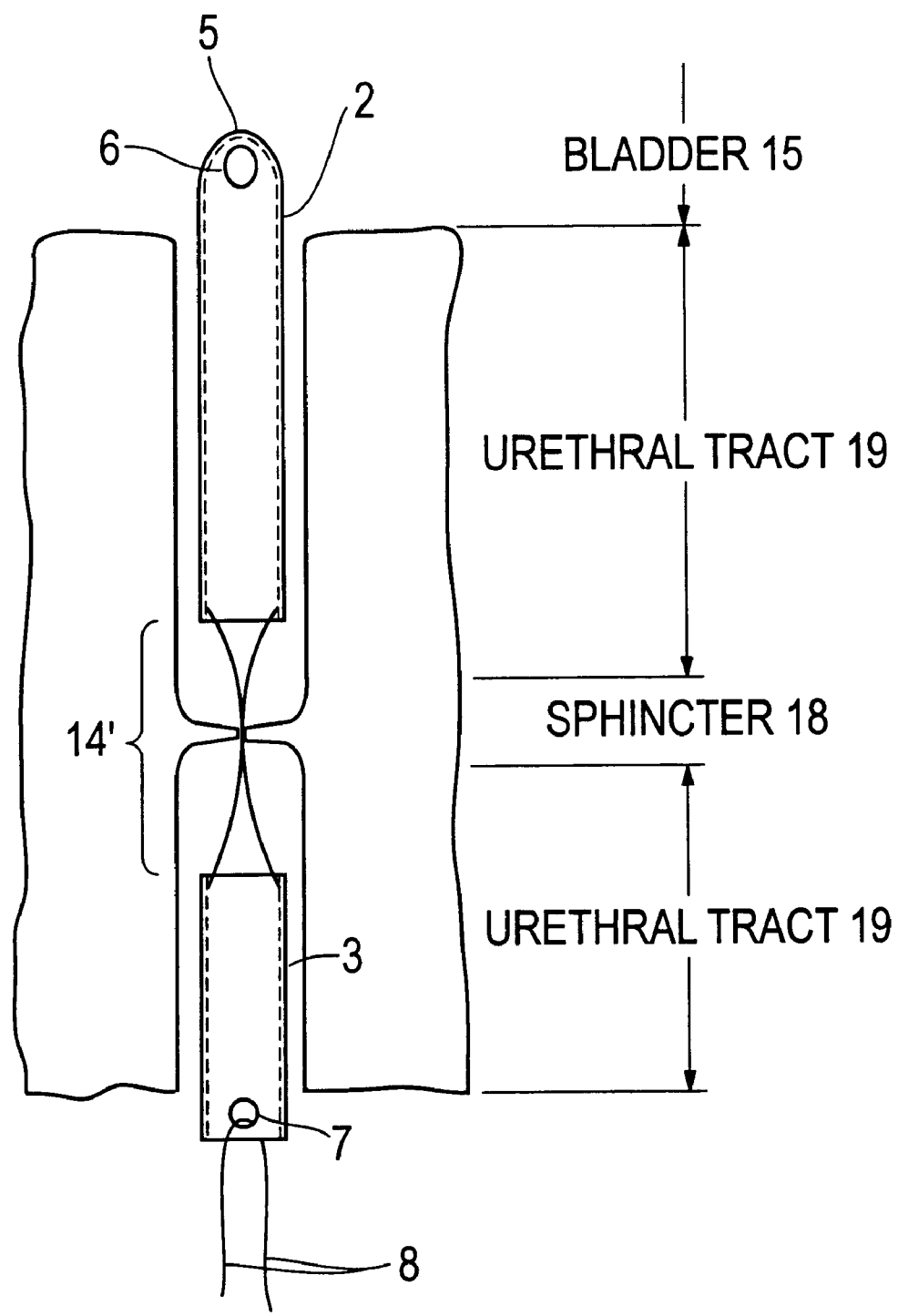

FIGS. 13–15 show a second exemplary embodiment of a stent assembly 200 and a third exemplary embodiment of the self-stabilizing prosthetic stent 1 according to this invention. As shown in FIGS. 13–15, this third exemplary embodiment of the self-stabilizing prosthetic stent 1 is usable with a second exemplary embodiment of a stent insertion and withdrawal method according to this invention.

In the third exemplary embodiment of the self-stabilizing prosthetic stent 1, as shown in FIGS. 13–15, the self-stabilizing prosthetic stent 1 includes the distal stent segment 2 having an orifice or opening 6 formed in the generally closed end 5 that permits fluid flow through the self-stabilizing prosthetic stent 1 when the generally closed end 5 of the distal stent segment 2 reaches the target organ or body cavity. The proximal stent segment 3 is provided with an eyelet 7 from which one or more withdrawal threads, pull-wires, or other equivalent structures 8 extend. A flexible connecting structure, such as, for example, a thin wire flexible connecting structure 14", joins the distal and proximal stent segments 2 and 3.

In addition, the stent assembly 200 includes a delivery catheter 20 having a first hollow tubular segment 22 of a cross-section less than that of a second hollow tubular segment 24. A stiff member 29 is provided to control the position of the distal stent segment 2 of the self-stabilizing prosthetic stent 1 after the distal stent segment 2 has reached the desired target organ or body cavity.

The second exemplary embodiment of the methods for inserting and withdrawing the self-stabilizing prosthetic stent 1 using the stent assembly 200 is shown in FIGS. 13–15. The self-stabilizing prosthetic stent 1 is mounted upon the first hollow tubular segment 22 of the delivery catheter 20 of the stent assembly 200. The self-stabilizing prosthetic stent 1 is mounted such that the distal stent segment 2 and the proximal stent segment 3 do not abut one another. A stiff member 29, which is provided through the first and second hollow tubular segments 22 and 24 of the delivery catheter 20 and through the distal and proximal stent segments 2 and 3 and the flexible connecting structure 14", maintains the distal and proximal stent segments 2 and 3 in non-abutting fashion relative to one another during insertion of the stent 1 into the anatomical tract.

The non-abutting relationship of the distal and proximal stent segments 2 and 3 during the insertion method of the second exemplary embodiment permits the flexible connecting structure 14" to be at least partially extended, though it need not be taut, throughout the insertion process of the stent 1 into the anatomical tract. FIGS. 13–15 shows the flexed status of the flexible connecting structure 14" as indicated by the curved, flexed thin wires of the flexible connecting structure 14".

The stent 1 is mounted upon the delivery catheter 20 such that a smaller diametered first hollow tubular segment 22 of the delivery catheter 20 is ensleeved by the distal stent segment 2, the at least partially extended flexible connecting structure 14", and the proximal stent segment 3. A trailing end of the proximal stent segment 3 rests on a shoulder of a second hollow tubular segment 24 having a diameter larger than that of the first hollow tubular segment 22. The shoulder of the second hollow tubular stent segment 24 advances the stent 1 into the anatomical tract by maintaining contact with the proximal stent segment 3 during insertion of the stent 1 into the anatomical tract.

Because of the non-abutting relationship of the distal and proximal segments 2 and 3, the flexible connecting structure 14" joining the distal and proximal stent segments 2 and 3 is at least partially extended, though not taut, as indicated by the curved, flexed status of the thin wires of the flexible connecting structure 14" in FIGS. 13–15.

The at least semi-rigid quality of the first hollow tubular segment 22 spans across the anatomical constricting structure, such as, for example, the sphincter 18 as the self-stabilizing prosthetic stent 1 is inserted into the anatomical tract, such as, for example, the urethra 19. By spanning across the anatomical constricting structure, such as, for example, the sphincter 18, the sphincter 18 and the flexible connecting structure 14" remain open for fluid to flow through the orifice or opening 6 into the distal stent segment 2, the flexible connecting structure 14", the proximal stent segment 3, and the delivery catheter 20 when the generally closed end 5 of the distal stent segment 2 reaches the target organ, such as, for example, the bladder 15.

Once fluid flow through the self-stabilizing prosthetic stent 1 and delivery catheter 20 is detected, the self-stabilizing prosthetic stent 1 has reached the target organ and/or body cavity, such as, for example, the bladder 15. A stiff member 29 is provided through the first and second hollow tubular segments 22 and 24 of the delivery catheter 20 to hold the distal stent segment 2 in place until the delivery catheter 20 is withdrawn.

As shown in FIG. 14, the delivery catheter 20 is then withdrawn to below the anatomical constricting structure, such as, for example, the sphincter 18. The flexible connecting structure 14" is then subject to the naturally occurring relaxing and constricting actions of the sphincter 18, such that fluid flow through the self-stabilizing prosthetic stent 1 and the delivery catheter 20 stops or slows. The stopping or slowing of fluid flow indicates the flexible connecting structure 14" is appropriately seated within the sphincter 18 region. More specific placement of the flexible connecting structure 14" may be achieved by gently tugging on at least one of the withdrawal threads, pull-wires, or other equivalent structures 8 until fluid flow stops completely, or is otherwise voluntarily controlled by the patient.

Thereafter, as shown in FIG. 15, the delivery catheter 20 is fully withdrawn and then the stiff member 29 is withdrawn, leaving the properly placed self-stabilizing prosthetic stent 1 in the anatomical tract, such as, for example, the urethra 19 such that the natural functioning of the anatomical constricting structure, such as, for example, the sphincter 18 is maintained.

It should be appreciated that the non-abutting relationship of the distal and proximal stent segments 2 and 3 could be achieved instead by friction fitting the distal stent segment 2 and proximal stent segment 3 onto the first hollow tubular segment 22 using an adjustable diametered first hollow tubular segment, releasable distal and proximal stent segment position holding structures, or other equivalent structures to hold the distal stent segment 2 and proximal stent segment 3 in place in non-abutting relation relative to one another during insertion of the stent 1 into the anatomical tract. After insertion of the stent 1, the delivery catheter could then be removed by reducing the diameter so that friction fitting no longer exists, or the release structures or other equivalent structures could be operated to permit withdrawal of the delivery catheter.

Withdrawal of the self-stabilizing prosthetic stent 1 is accomplished as in the earlier exemplary embodiments by tugging sufficiently on at least one of the withdrawal threads, pull-wires, or other equivalent structures 8 to overcome the anatomical constricting forces of the anatomical constricting structure, such as, for example, the sphincter 18. Having overcome the anatomical constricting forces, the self-stabilizing prosthetic stent 1 is freely removable from the anatomical tract, such as, for example, the urethral tract 19.

Figure 16:
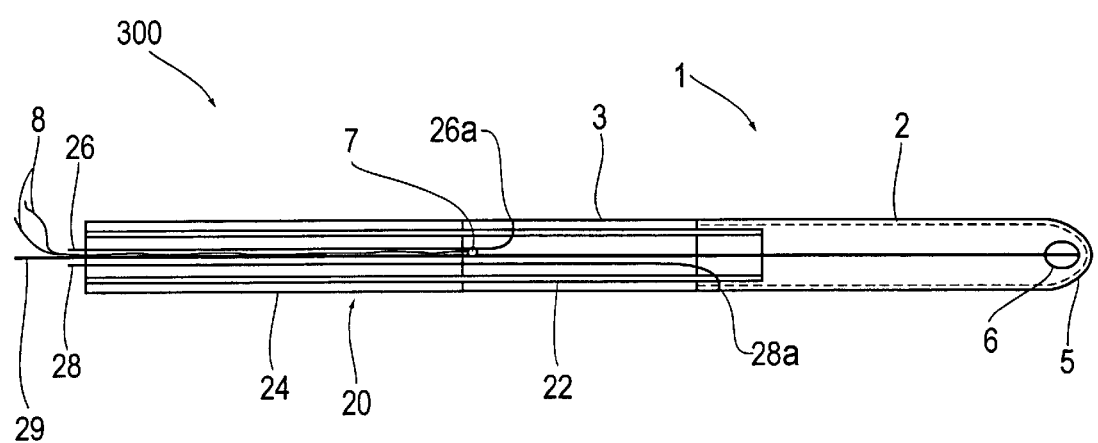
FIG. 16 illustrates a third exemplary embodiment of the stent assembly according to this invention.

FIG. 16 illustrates a third exemplary embodiment of a stent assembly 300 and an exemplary embodiment of the stent 1 according to this invention. As shown in FIG. 16, this third exemplary embodiment of the stent assembly 300 accommodates the third and fourth exemplary embodiments of the stent insertion and withdrawal methods according to this invention, as shown in FIGS. 16–25.

In the third exemplary embodiment of the stent assembly 300, as shown in FIG. 16, the self-stabilizing prosthetic stent 1 again includes the distal segment 2 having the orifice or opening 6 for permitting fluid flow through the self-stabilizing prosthetic stent 1, the proximal stent segment 3, the one or more withdrawal threads, pull-wires, or other equivalent structures 8, and one of the flexible connection structures 4 or 14 as outlined above. In addition, the third exemplary embodiment of the stent assembly 300 shown in FIG. 16 includes the delivery catheter 20, a proximal segment release structure 26, a distal segment release structure 28, and the stiff member 29. In general, the stiff member 29 is usable to control the position of the distal segment 2 of the self-stabilizing prosthetic stent 1.

In various exemplary embodiments, the delivery catheter 20 includes the two tubular segments 22 and 24. The first segment 22 has a cross-section that is less than the cross-section of the second segment 24 and that is less than the cross-section of the distal and proximal segments 2 and 3. Thus, the stent 1 is mounted upon the first segment 22 of the delivery catheter 20 for inserting the stent 1 into an anatomical tract such that the generally closed end 5 of the distal segment 2 of the stent 1 enters the anatomical tract first as the self-stabilizing prosthetic stent 1 is inserted to the anatomical tract.

An end 28a of the distal segment release structure 28 protrudes through the wall of the delivery catheter 20 to hold the distal segment 2 relative to the first tubular segment 22 as the stent assembly 300 is used to advance the stent 1 into position in the anatomical tract. Similarly, an end 26a of the proximal segment release structure 26 protrudes through the wall of the delivery catheter 20 to hold the proximal segment 3 relative to the second tubular segment 24 as the stent assembly 300 is used to advance the stent 1 into position in the anatomical tract.

The distal and proximal segment release structures 28 and 26, respectively, hold the distal and proximal segments 2 and 3, respectively, relative to the delivery catheter 20 such that the distal and proximal segments 2 and 3 approximately abut one another when the self-stabilizing prosthetic stent 1 is mounted on the delivery catheter 20 to form stent assembly 300. This causes the flexible connecting structure 4 or 14 to take a collapsed state, especially as the stent 1 is inserted into the anatomical tract. As a result, relative to the first and second exemplary embodiments of the stent assembly 100 and 200, the third exemplary embodiment of the stent assembly 300, because the distal segment 2 of the stent 1 approximately abuts the proximal segment 3 of the stent 1, provides an outer surface of the stent 1 as a part of the stent assembly 300 that is relatively smoother and more continuous.

Once inserted through the anatomical tract, such as, for example, a urethral tract 19, as shown schematically in FIGS. 17–25, the distal segment 2 is maintained in place relative to the target organ and/or body cavity by the stiff member 29 projecting through the delivery catheter 20 and through the stent 1. That is, the stiff member 29 contacts a portion of the generally closed end 5 of the stent 1 to hold the stent in place relative to the targeted organ or body cavity, such as, for example, the bladder 15. Fluid flow through the lateral orifice or opening 6 of the distal segment 2 once again indicates that the stent 1 has been placed in the desired position adjacent to or extending into the target body organ or body cavity, such as, for example, the bladder 15.

Figure 17:
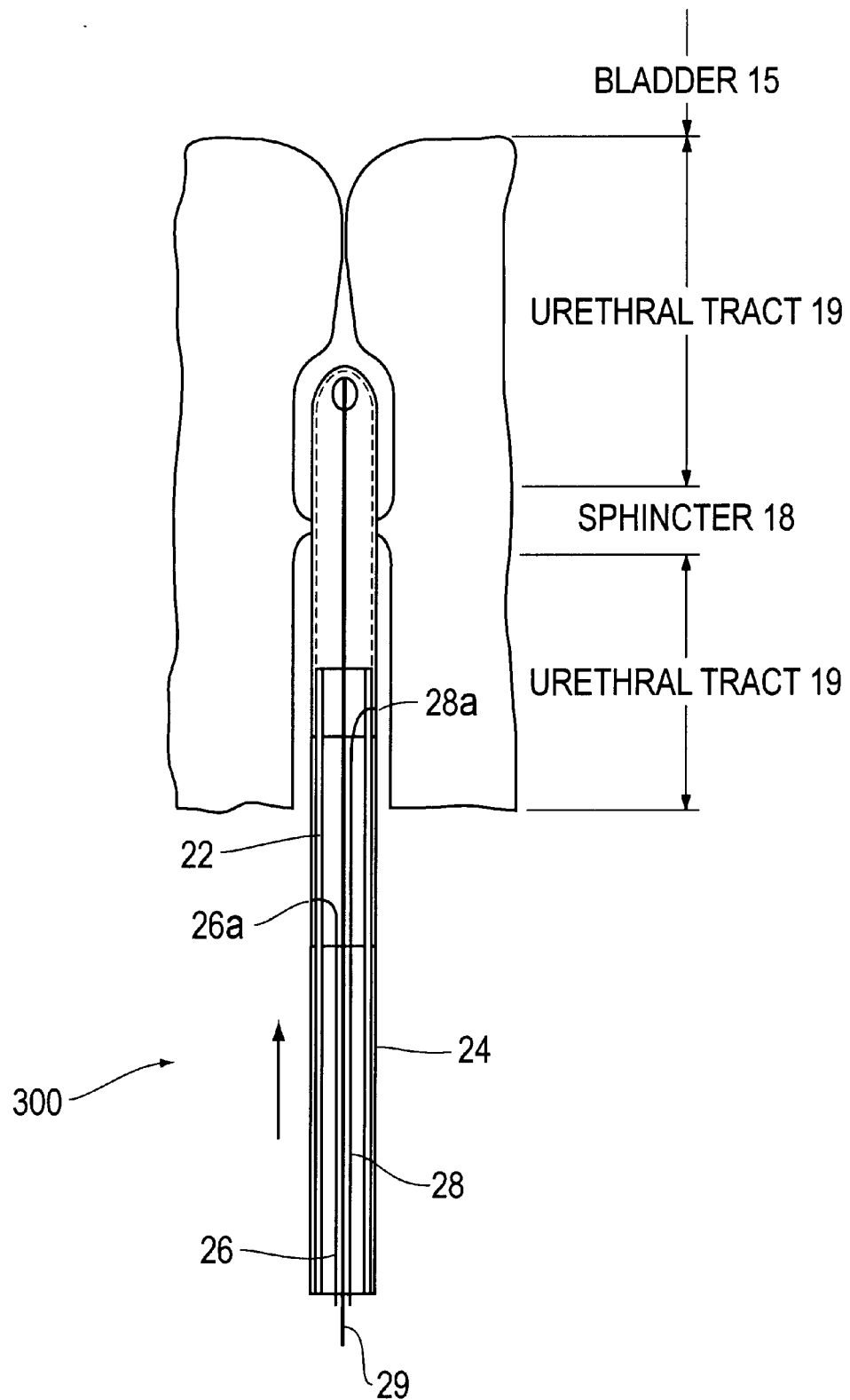
FIGS. 17–20 illustrate a third exemplary embodiment of a method for inserting a self-stabilizing prosthetic stent according to this invention using the third exemplary embodiment of the stent assembly of FIG. 16.

FIGS. 17–20 illustrate the insertion steps of a third exemplary embodiment of the method according to this invention of inserting the stent 1 using the third exemplary embodiment of the stent assembly 300. As shown in FIG. 17, the stent 1 is mounted upon the first segment 22 of the delivery catheter 20 such that the distal and proximal segments 2 and 3 abut due to the collapsed state of the flexible connecting structure 4 or 14. The generally closed end 5 of the distal segment 2 of the stent 1 enters the anatomical tract first. The distal release structure 28 maintains the position of the distal segment 2 relative to the delivery catheter 20 during insertion using the end 28a that protrudes through the wall of the delivery catheter 20. The proximal release structure 26 maintains the position of the proximal segment 3 relative to the delivery catheter 20 during insertion using the end 26a that protrudes through the wall of the delivery catheter. The ends 26a and 28a of the proximal and distal release structures 26 and 28 thus maintain the proximal and distal segments 3 and 2 in the abutting relation during insertion. The abutting relation of the proximal and distal segments 3 and 2 is maintained until one or both of the proximal and distal release structures 26 and 28 is removed from the delivery catheter 20 after the stent 1 is inserted.

Figure 18:
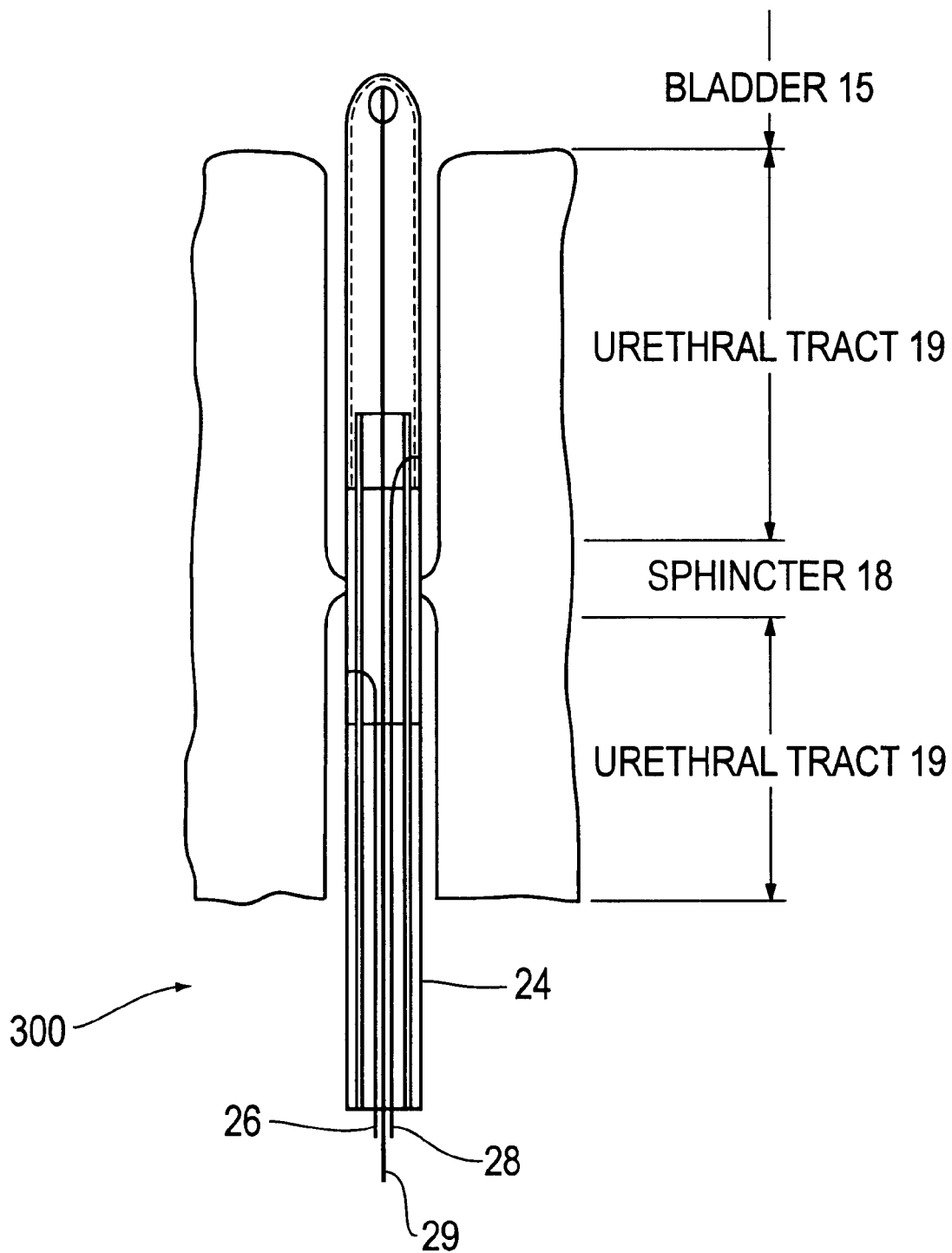

As shown in FIG. 18, the stent 1 is fully inserted through the anatomical tract 19 such that the stent 1 reaches a target organ or cavity, such as, for example, the bladder 15. In particular, in this third exemplary embodiment of the method, the distal segment 2 is positioned entirely above the anatomical constricting structure, such as, for example, the sphincter 18. A flow of fluid through the orifice or opening 6 of the distal segment 2 of the stent 1 and delivery catheter 20 indicates the stent 1 has reached the target organ or body cavity, such as, for example, the bladder 15.

Figure 19:
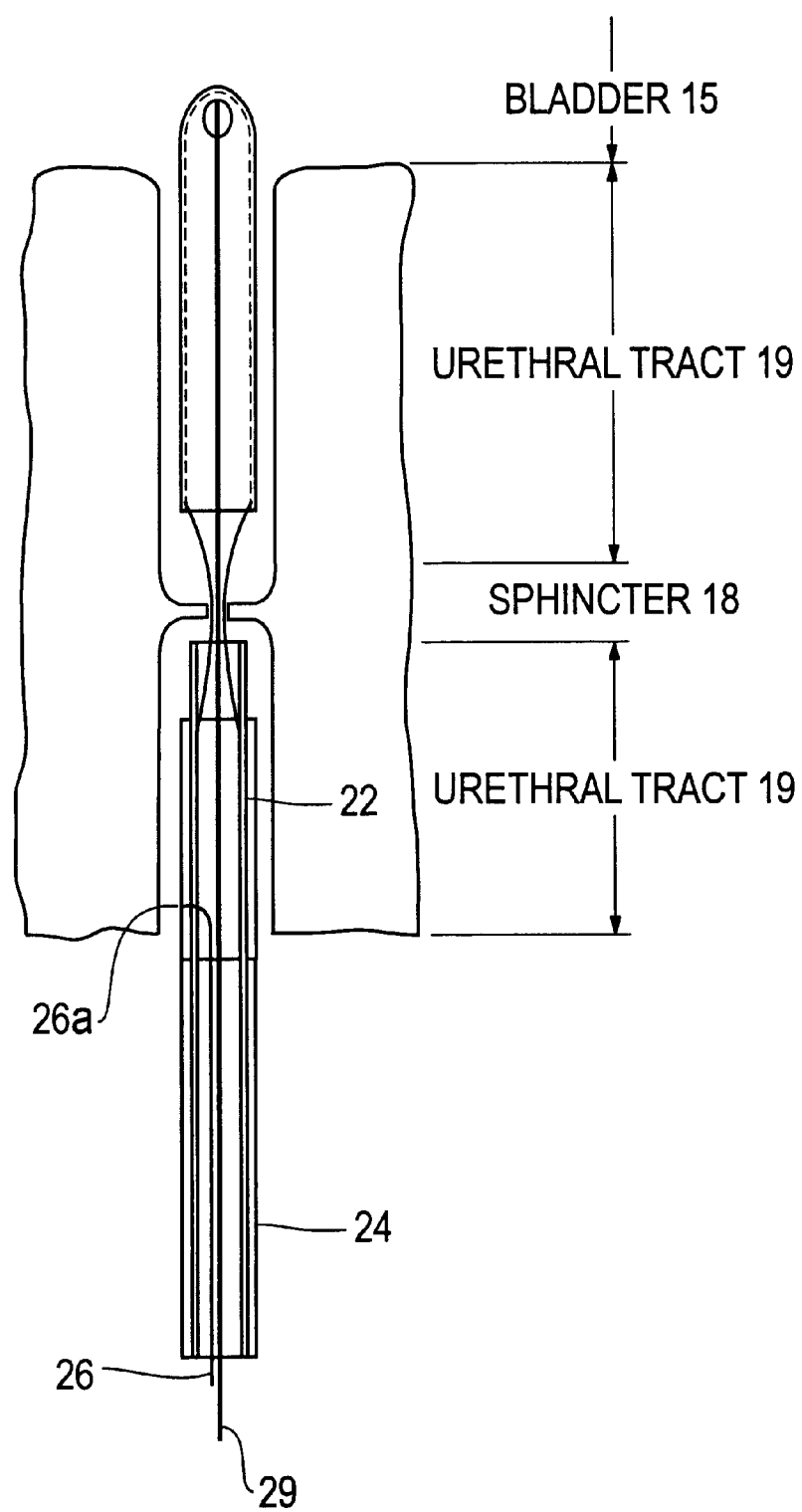

Thereafter, as shown in FIG. 19, the distal segment release structure 28 is removed. As a result, the distal segment 2 is released from the delivery catheter 20. The stiff member 29 remains in position stabilizing the distal segment 2. Thus, the delivery catheter 20 can be withdrawn without affecting the position of the distal segment 2. Next, either at the same time or at some time thereafter, the delivery catheter 20 is incrementally withdrawn to below the sphincter 18. The withdrawal of the distal segment release structure 28 from the stent assembly 300 and the incremental withdrawal of the delivery catheter 20 to below the sphincter 18 permits the flexible connection structure 4 or 14 to extend from the collapsed state and to assume a position in the region of the anatomical constricting structure, such as, for example, the sphincter 18. The flexible quality of the connecting structures 4 or 14 permits the natural relaxing and constricting functions of the anatomical constricting structure, such as, for example, the muscles of the sphincter 18, to occur. As a result, the flow of fluid through the stent 1 and delivery catheter 20 ceases, or is otherwise voluntarily controlled by the patient. The ability of the patient to stop, or otherwise control the fluid flow indicates the stent 1 is appropriately positioned within the anatomical tract 19 and across the anatomical constricting structure, such as, for example, the sphincter 18.

Figure 20:
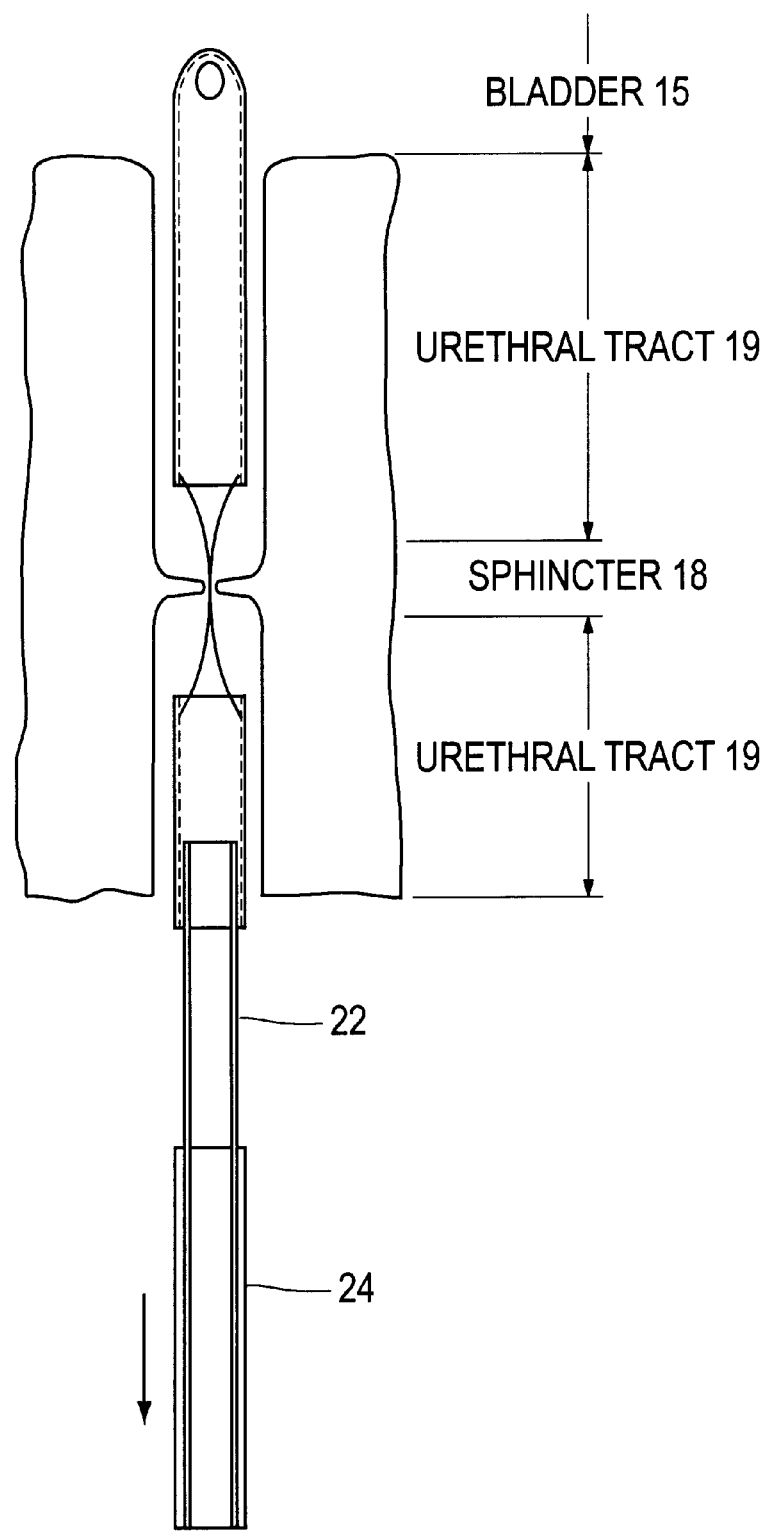

Thereafter, as shown in FIG. 20, the stiff member 29 is withdrawn. As also shown in FIG. 20, the proximal segment release structure 26 is also withdrawn. As a result, the proximal segment 3 is released from the delivery catheter 20. Thus, the delivery catheter 20 and the proximal stent segment 3 can move within the anatomical tract relative to one another. This permits the flexible connection structure 4 or 14 to more fully extend and seat itself within the anatomical constricting structure, such as, for example, the sphincter 18.

Finally, as also shown in FIG. 20, the delivery catheter 20 is completely withdrawn from the anatomical tract 19. As a result, the stent 1 remains in the anatomical tract 19 as an artificial passage having the flexible connecting structure 4 or 14 that is compliant with the natural constricting functions of, for example, the sphincter 18.

Figure 21:
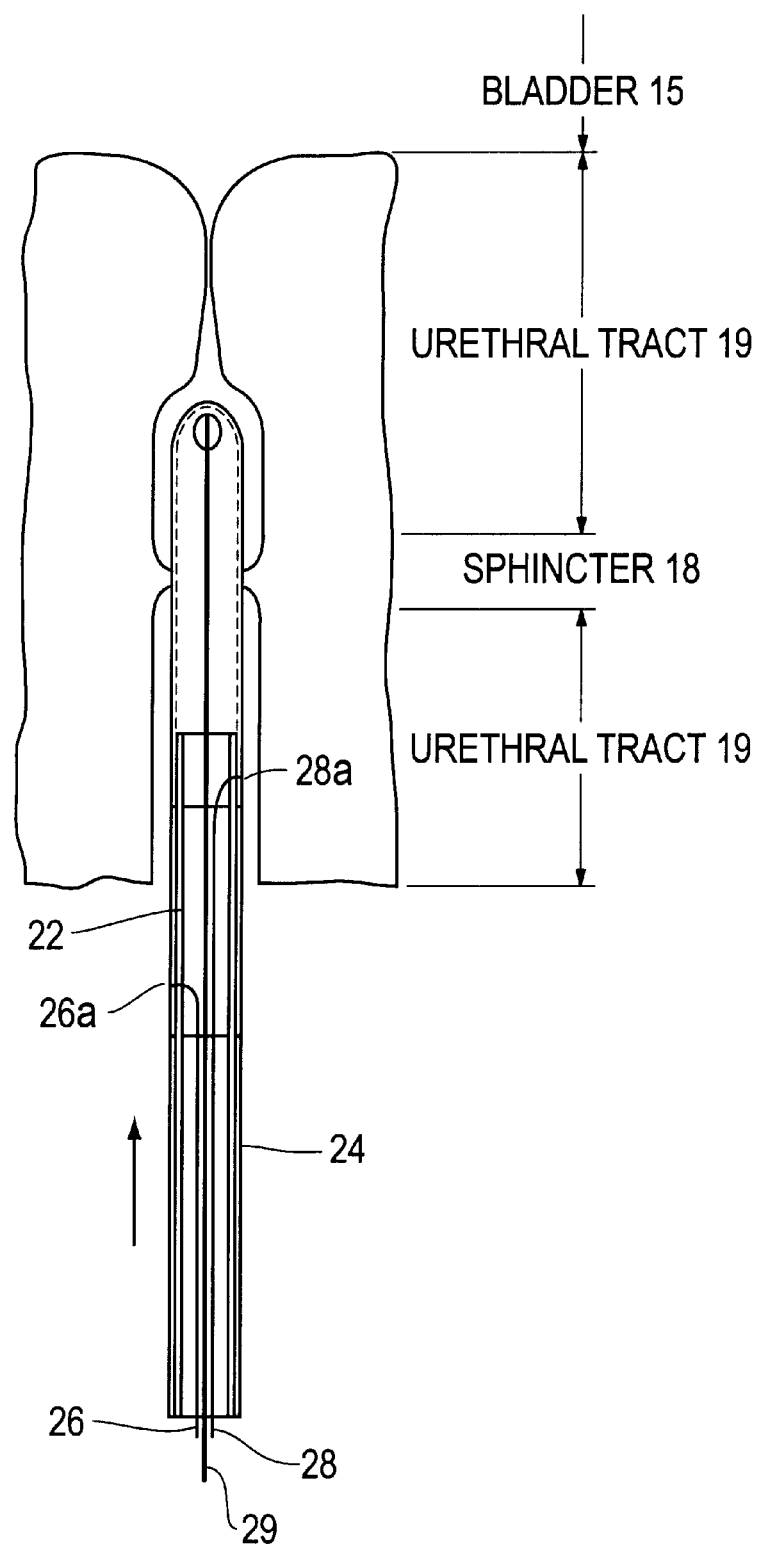
FIGS. 21–25 illustrate a fourth exemplary embodiment of a method for inserting a self-stabilizing prosthetic stent according to this invention using the third exemplary embodiment of the stent assembly of FIG. 16.

FIGS. 21–25 shows a fourth exemplary embodiment of the method of inserting the stent according to this invention. As shown in FIG. 21, the stent 1 is mounted upon the first segment 22 of the delivery catheter 20 such that the distal and proximal segments 2 and 3 abut due to the collapsed state of the one of the flexible connecting structures 4 or 14. Again, the generally closed end 5 of the distal segment 2 of the stent 1 enters the anatomical tract first. The distal release structure 28 maintains the position of the distal segment 2 relative to the delivery catheter 20 during insertion using the end 28a that protrudes through the wall of the delivery catheter 20. The proximal release structure 26 maintains the position of the proximal segment 3 relative to the delivery catheter 20 during insertion using the end 26a that protrudes through the wall of the delivery catheter. The ends 26a and 28a of the proximal and distal release structures 26 and 28 thus maintain the proximal and distal segments 3 and 2 in abutting relation during insertion. The abutting relation of the proximal and distal segments 3 and 2 is maintained until one or both of the proximal and distal release structures 26 and 28 is removed from the delivery catheter 20 after the stent 1 is at least partially inserted.

Figure 22:
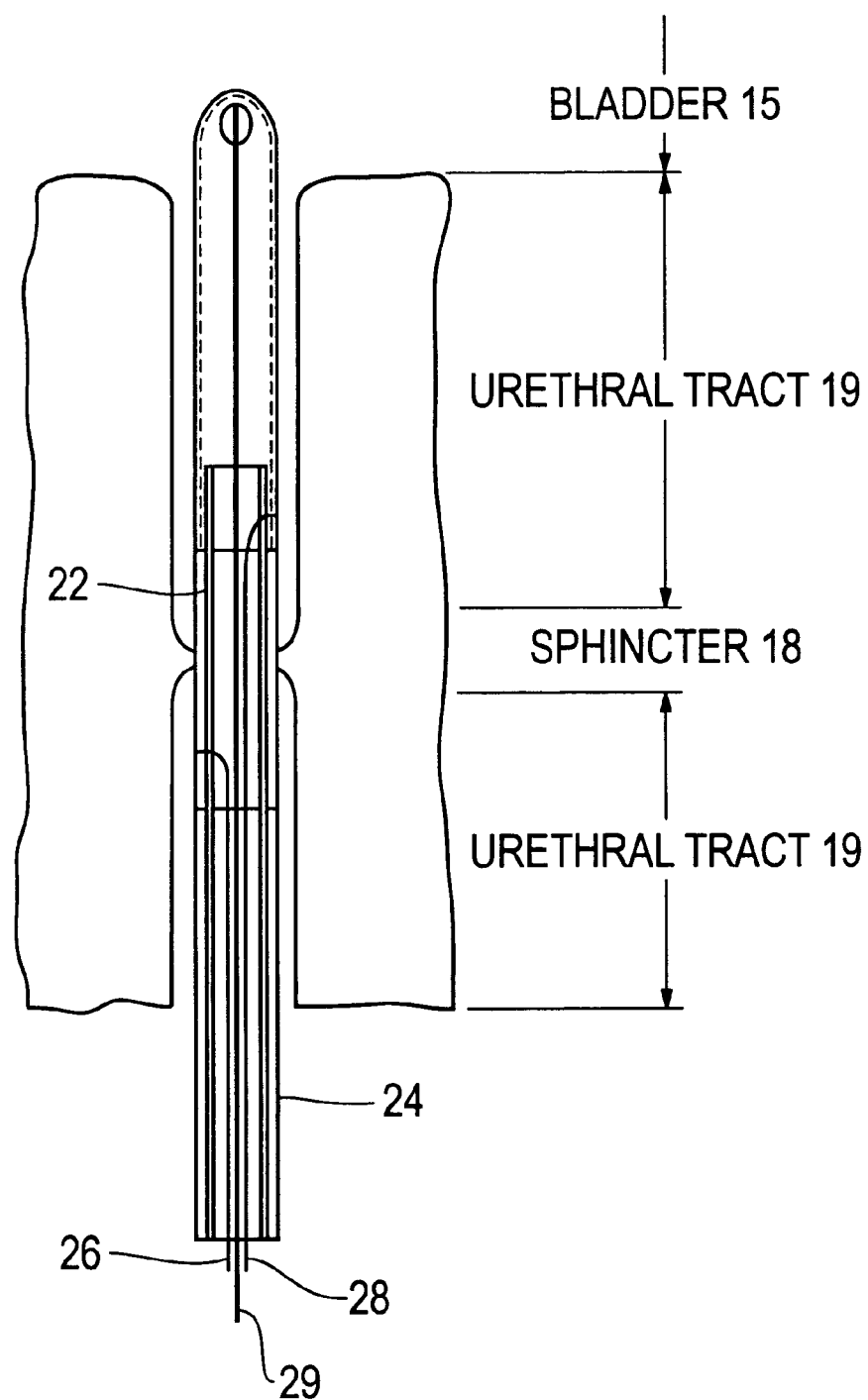

As shown in FIG. 22, the stent 1 is fully inserted through the anatomical tract 19 such that the stent 1 reaches the target organ or body cavity, such as, for example, the bladder 15, and the distal segment 2 is positioned entirely above the anatomical constricting structure, such as, for example, the sphincter 18. Again, the flow of fluid through the orifice or opening 6 of the distal segment 2 of the stent 1 and the delivery catheter 20 indicates the stent 1 has reached the target organ or body cavity, such as, for example, the bladder 15.

Figure 23:
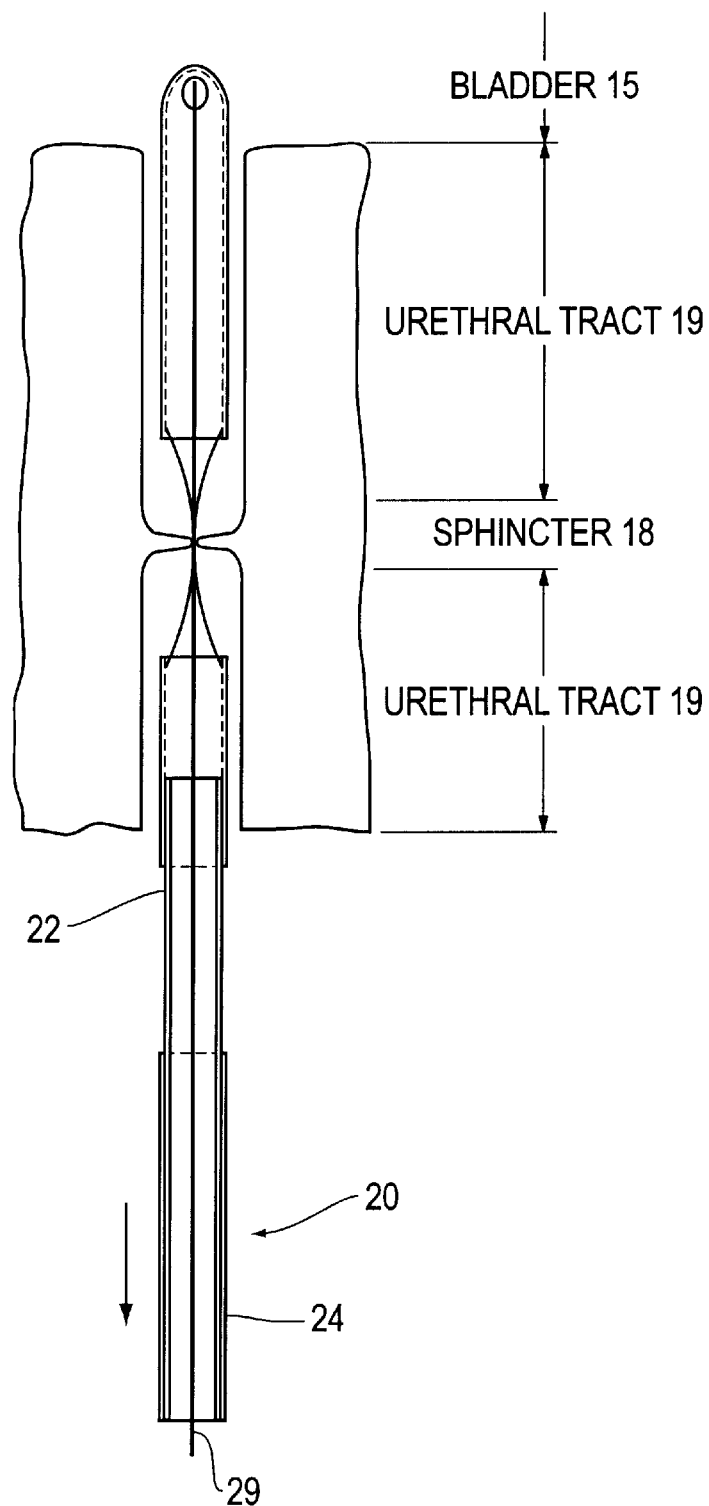

Thereafter, as shown in FIG. 23, the distal and proximal segment release structures 28 and 26 are removed in sequence. The distal and proximal stent segment release structures 28 and 26 are not removed simultaneously. This method is like the previous method, except that the delivery catheter is removed first, followed by the stiff member 29. Thus, once initial fluid or gas flow demonstrates that the anatomical cavity has been attained, the distal stent segment release structure 28 is removed. Stabilized by the stiff member 29, the distal stent segment 2 remains in position while the proximal stent segment 3, still mounted on the delivery catheter 20, is withdrawn to a position proximal to the sphincter 18. When the patient can demonstrate voluntary control of micturition, then the proximal stent release structure 26 is removed. Now, in distinction to the prior method, the stiff member 29 remains while the delivery catheter is withdrawn, followed by removal of the stiff member 29.

The release of the proximal and distal release segment structures 26 and 28, and the incremental release of the delivery catheter 20 to below the sphincter 18 permits the flexible connecting structure 4 or 14 to relax from its collapsed state such that the connecting structure 4 or 14 assumes a position in the region of, for example, the sphincter 18. The flexible connecting structure 4 or 14, when positioned within the region of the sphincter 18, permits the natural relaxing and constricting functions of the anatomical constricting structure, such as, for example, the muscles of the sphincter 18, to occur. As a result, fluid flow through the stent 1 and delivery catheter 20 ceases, or is otherwise voluntarily controlled by the patient. The ceasing, or patient control of the fluid flow, indicates that the stent 1 and the flexible connecting structure 4 or 14 are appropriately placed within the anatomical tract 19 such that the stent 1 provides an artificial passage through the anatomical tract 19.

Figure 24:
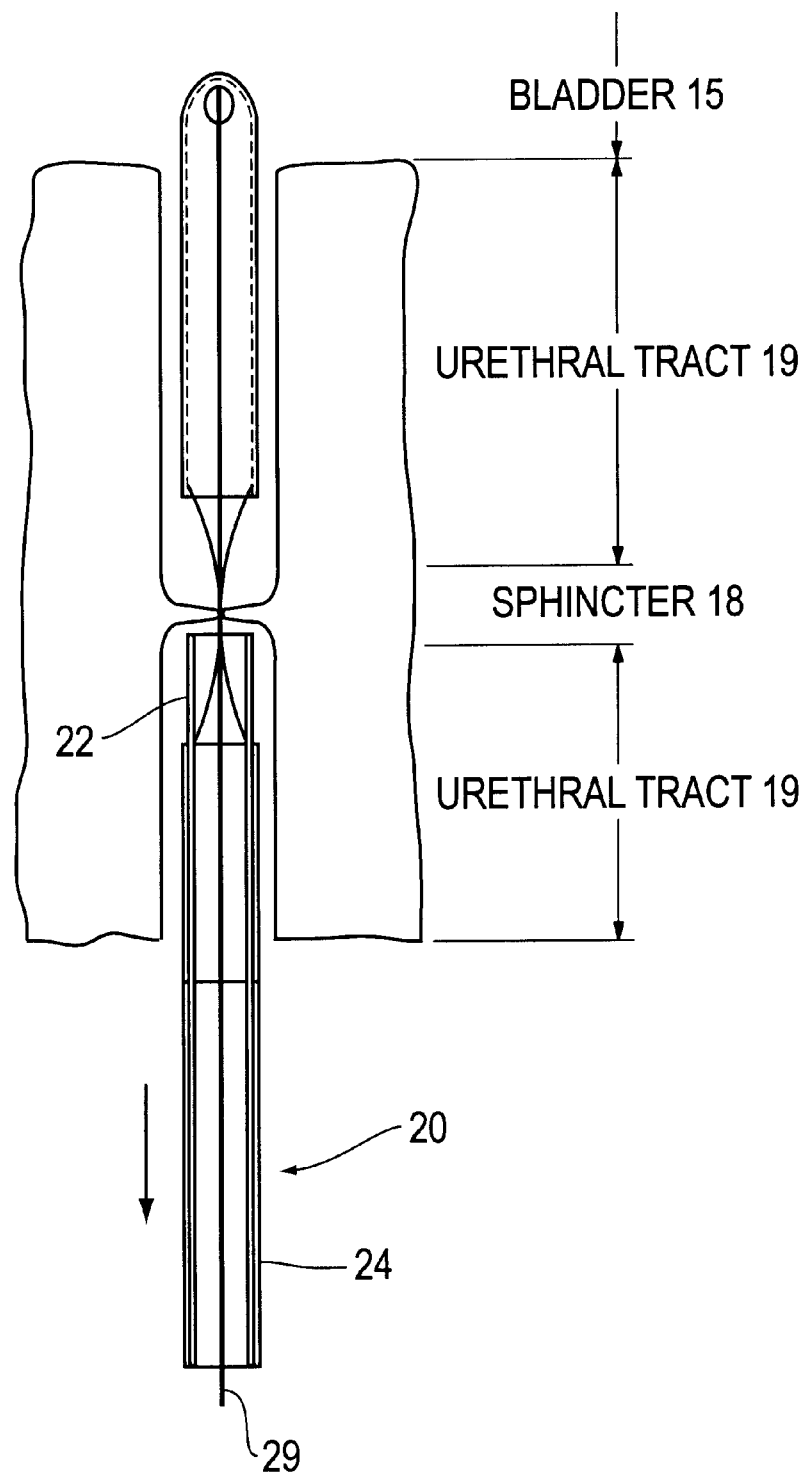

Thereafter, as shown in FIG. 24, the delivery catheter 20 is completely withdrawn from the anatomical tract 19 permitting the flexible connecting structure 4 or 14 to fully extend or relax such that it seats even more compliantly within the musculature of the anatomical constricting structure, such as, for example, the sphincter 18. The stiff member 29 is maintained in position to keep the stent 1 from drifting or moving until all other components of the stent insertion assembly 300 are successfully withdrawn.

Figure 25:
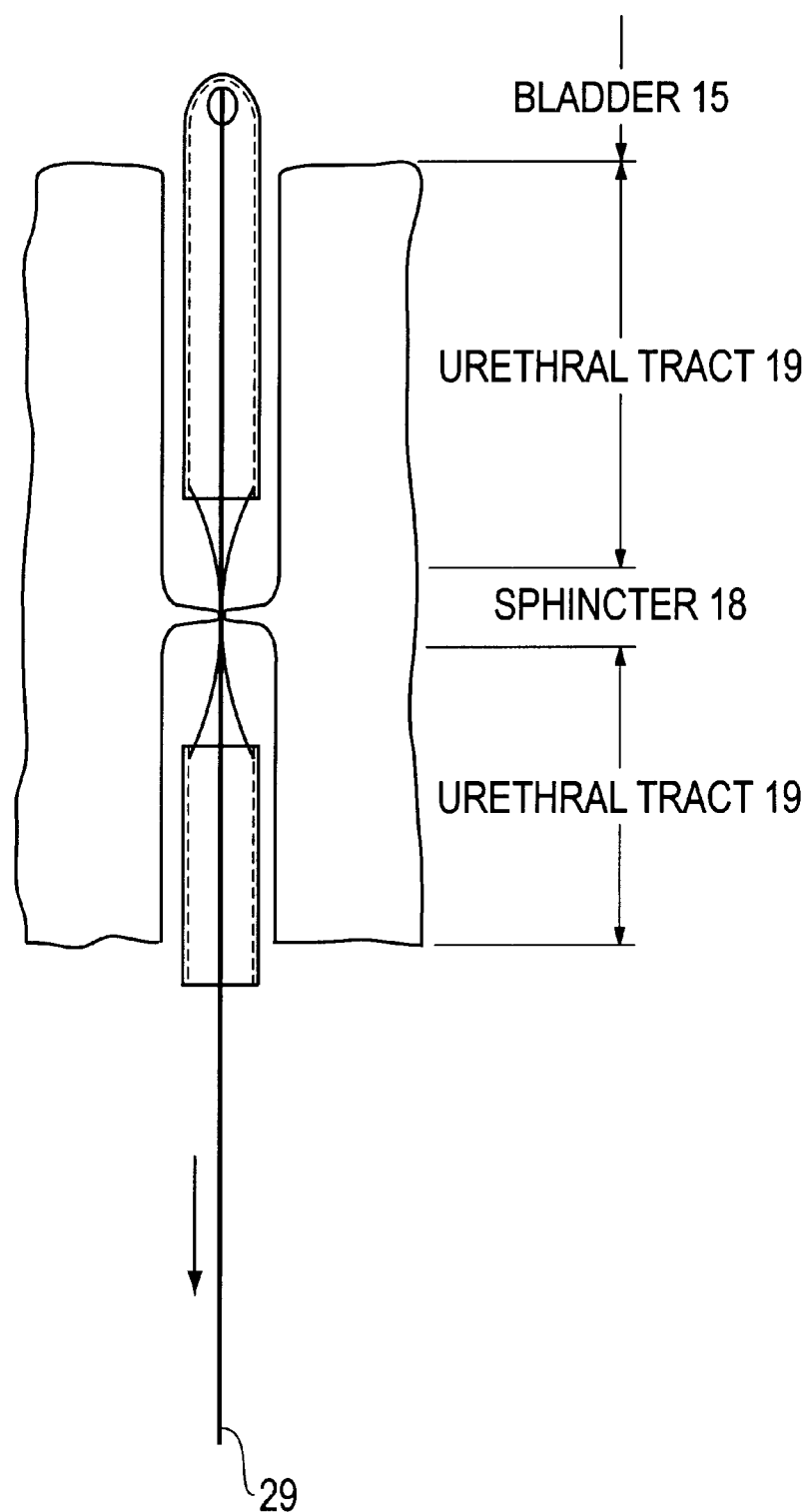

Finally, as shown in FIG. 25, the stiff member 29 is completely withdrawn from the anatomical tract 19.

Figure 26:
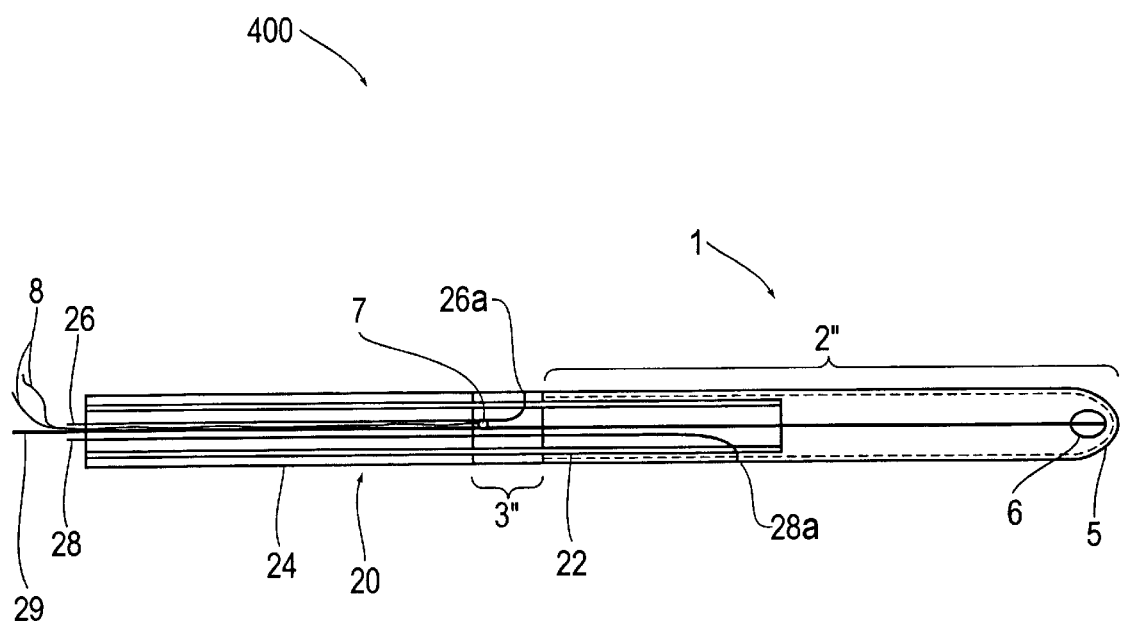
FIG. 26 illustrates a fourth exemplary embodiment of the stent assembly according to this invention.

FIG. 26 shows a fifth exemplary embodiment of a stent assembly 400 and another exemplary embodiment of the stent 1. As shown in FIG. 26, in this exemplary embodiment, the stent 1 has an elongated distal segment 2" as compared to the distal segment 2 of the third and fourth exemplary embodiments, and a truncated proximal segment 3" as also compared to the proximal segment 3 of the third and fourth exemplary embodiments.

Figure 27:
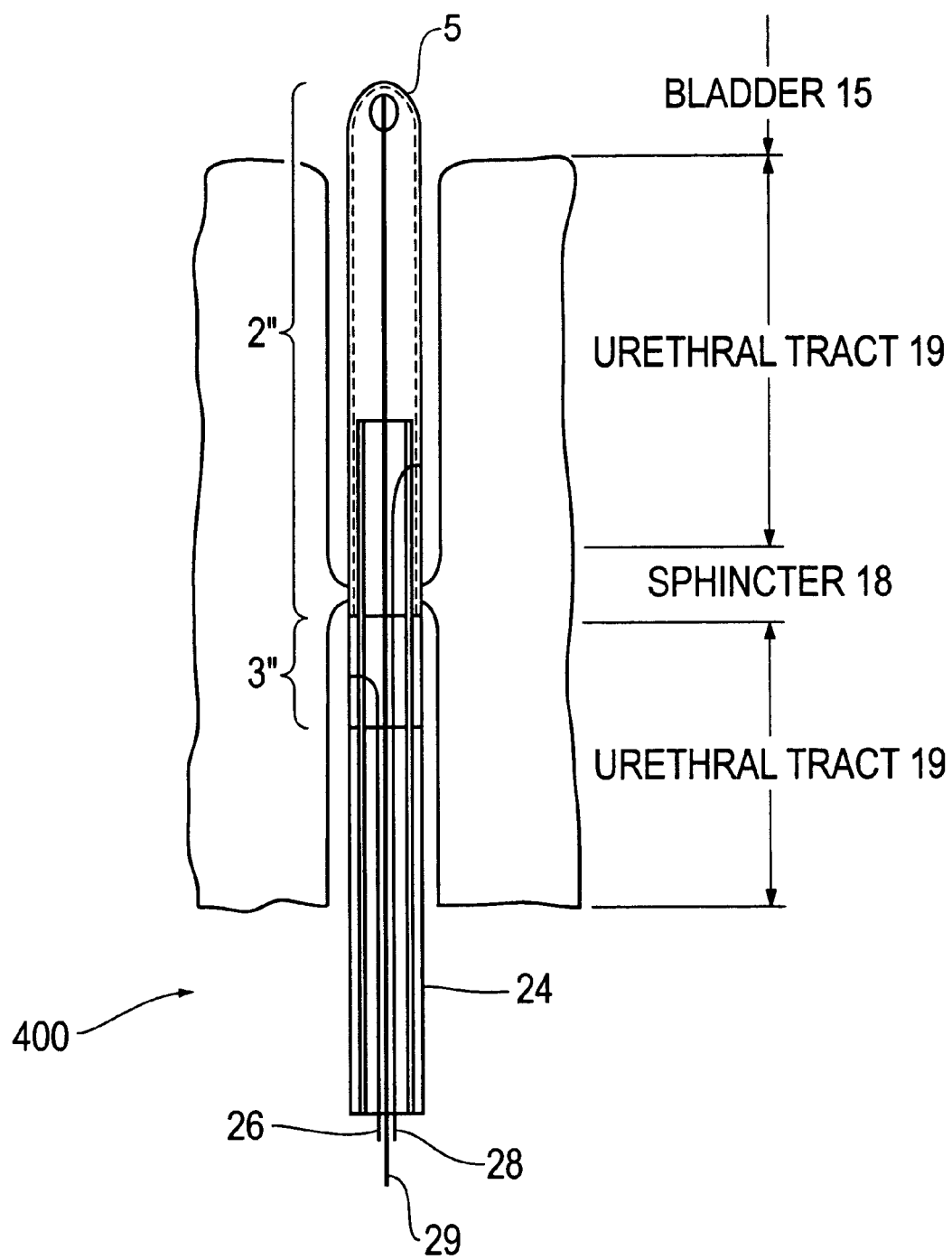
FIGS. 27–31 illustrate a fifth exemplary embodiment of a method for inserting a self-stabilizing prosthetic stent according to this invention using the fourth exemplary embodiment of the stent assembly of FIG. 26.
Figure 28:
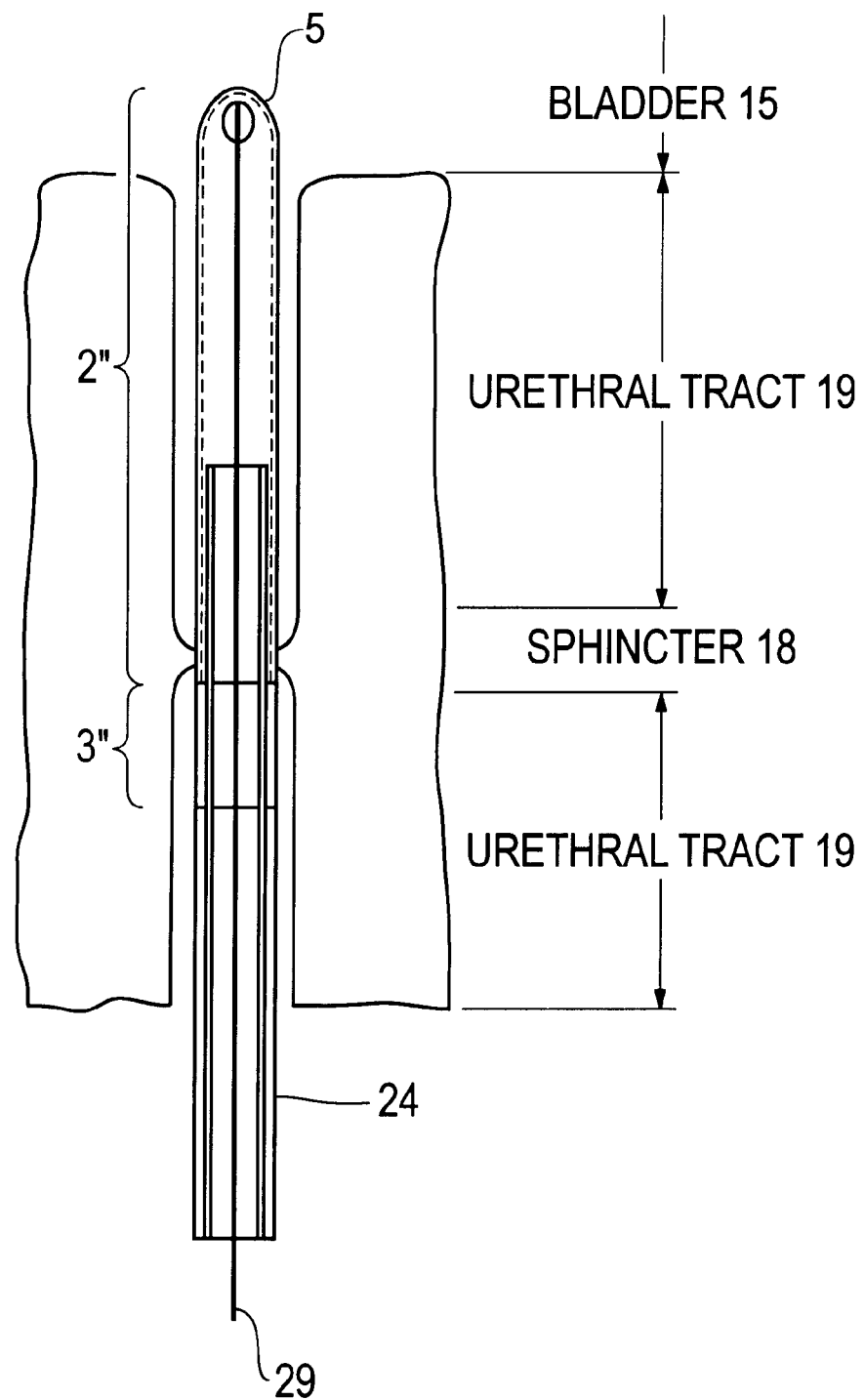

As shown in FIGS. 27 and 28, the elongated distal segment 2" permits the distal segment 2" to penetrate a target organ and/or body cavity, such as, for example, the bladder 15 while still spanning across the anatomical constricting structure, such as, for example, the sphincter 18 during insertion of the stent 1 to the anatomical tract. Because the elongated distal segment 2" spans the anatomical constricting structure, such as, for example, the sphincter 18, the flow of fluid from the target organ and/or body cavity, such as, for example, the bladder 15 is permitted to flow through the stent 1 and the delivery catheter 20 indicating the elongated distal segment 2" has reached, for example, the bladder 15.

FIGS. 27–31 show a fifth exemplary embodiment of a method for inserting a self-stabilizing prosthetic stent according to this invention. In this fifth exemplary embodiment, the stent 1 is initially inserted, with the distal and proximal segments 2 and 3 abutting one another, as shown in either of FIGS. 18 and 22.

Thus, as shown in FIG. 27, the elongated distal segment 2" is both positioned relative to the target organ or body cavity and holds open the anatomical constricting structure, such as, for example, the sphincter 18. As a result, the truncated proximal segment 3" lies entirely below the anatomical constricting structure, such as, for example, the sphincter 18. This is in contrast to the third and fourth exemplary embodiments described above, where the distal segment 2 lies entirely above the anatomical constricting structure and the proximal segment 3 holds the anatomical constricting structure open.

Thereafter, as shown in FIG. 28, the proximal and distal segment release structures 26 and 28 are withdrawn. Upon release of the proximal and distal segment release structures 26 and 28, the truncated proximal segment 3" and the elongated distal segment 2" are released from the delivery catheter 20. Thus, the delivery catheter 20 and the truncated proximal segment 3" and the elongated distal segment 2" can move within the anatomical tract relative one another.

Figure 29:
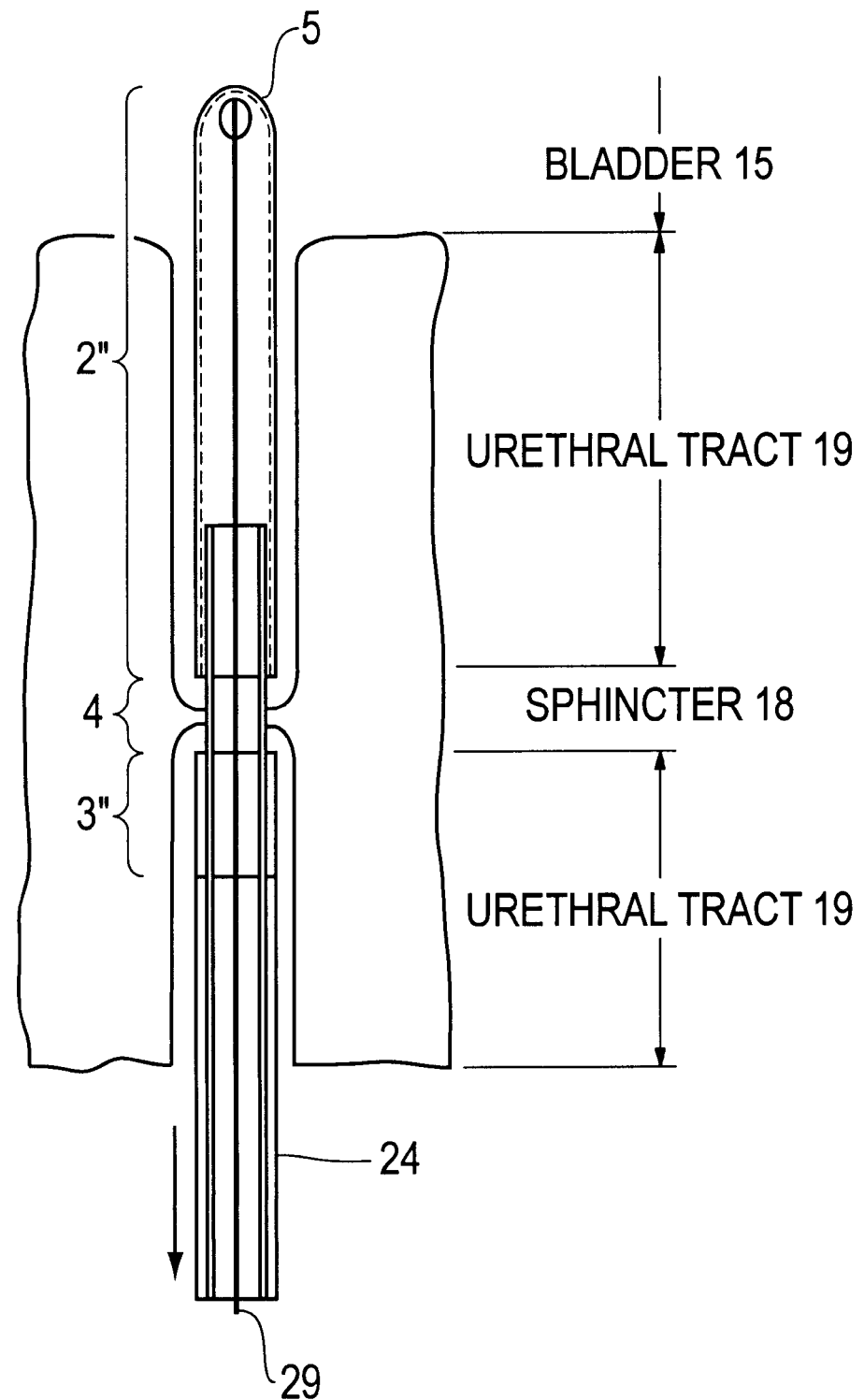

Next, as shown in FIG. 29, a stiff member 29 is used to advance the generally closed end 5 of the elongated distal segment 2" further upward relative to the target organ and/or body cavity, such as, for example, the bladder 15. As a result, the elongated distal segment 2" and the truncated proximal segment 3" no longer abut one another and the flexible connecting structure 4 extends to seat within the anatomical constricting structure, such as, for example, the sphincter 18. As shown in FIG. 29, the elongated distal stent segment 2" is moved upward so that it is entirely above the anatomical constricting structure, such as, for example, the sphincter 18. As a result, the flexible connecting structure 4 or 14 is relaxed from the collapsed state and located within the region of the anatomical constricting structure, such as, for example, the sphincter 18. The stiff member 29 is used to maintain the elongated distal stent segment 2" in position relative to the target organ and/or body cavity, for example, the bladder 15, while the other elements of the stent delivery assembly 400 are withdrawn.

Figure 30:
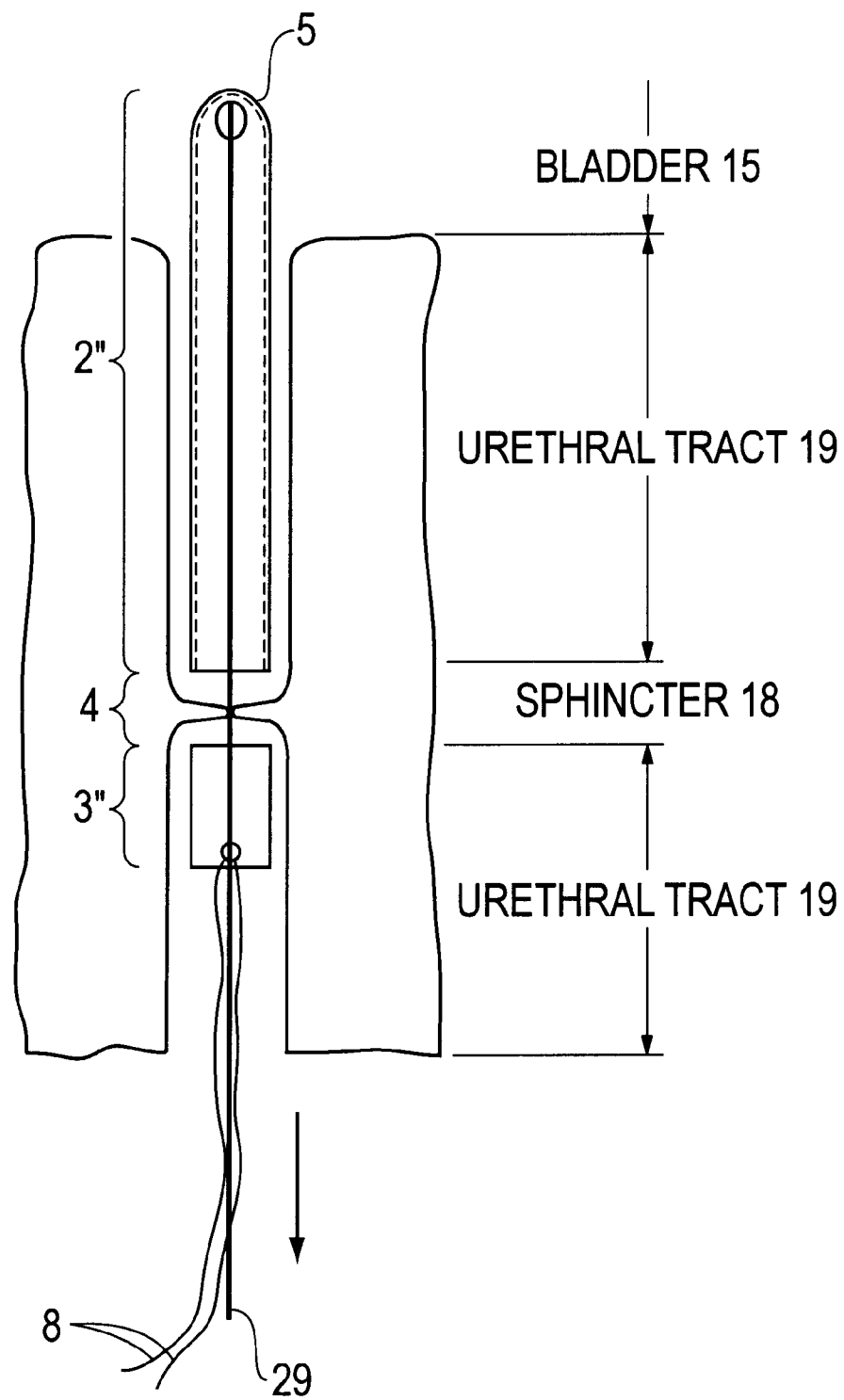

Thereafter, as shown in FIG. 30, the first and second tubular segments 22 and 24 of the delivery catheter 20 are withdrawn from the anatomical tract 19. As a result, the stiff member 29 holds the stent 1 in place to appropriately position the extended flexible connecting structure 4 within the anatomical constricting structure, such as, for example, the sphincter 18. As in earlier described embodiments, a gentle tugging on at least one of the withdrawal threads, pull-wires, or other equivalent structures 8 provide a more specific positioning of the flexible connecting structure 4 within the anatomical constricting structure, such as, for example, the sphincter 18.

Figure 31:
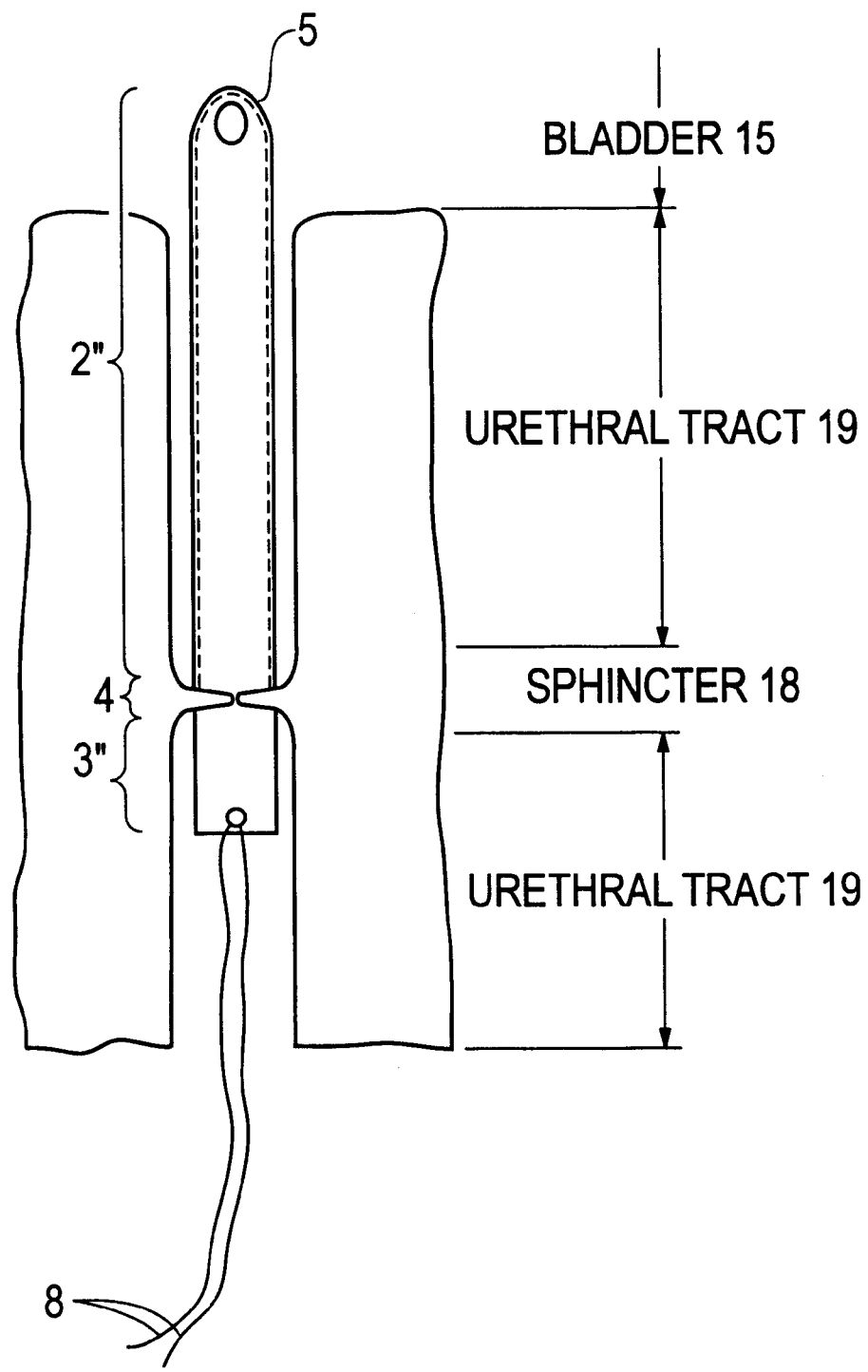

Then, as shown in FIG. 31, the stiff member 29 is removed. As a result, the self-stabilizing prosthetic stent 1 is securely and appropriately placed within the anatomical constricting structure, such as, for example, the sphincter 18 so that the flexible connecting structure 4 complies with the naturally occurring relaxing and constricting functions of, for example, the sphincter 18.

In either of the embodiments shown in FIGS. 16–31, withdrawing the stent 1 from the anatomical tract 19 is accomplished similar to that described in the first and second exemplary embodiments of the method. That is, a steady pulling force on at least one of the withdrawal threads, pull-wires, or other equivalent structures 8 overcomes the resistance of the muscles of the anatomical constricting structure, such as, for example, the resistance of the muscles of the sphincter 18 such that the stent 1 can slidingly descend through the anatomical tract 19 for removal.

It should further be appreciated that, in yet another embodiment, the elongated distal and truncated proximal stent segments 2" and 3" may be mounted in abutting relation to one another on first and second tubular segments 22' and 24' of the delivery catheter 20'. The first and second tubular segments 22' and 24' have substantially the same diameter. This is in contrast to the differing diameters of the first and second tubular segments 22 and 24 of earlier described embodiments. As a result, the stent 1 is inserted into the desired anatomical tract, such as, for example, the urethra 19 and across the anatomical constricting structure, such as, for example, the sphincter 18. The delivery catheter 20' prohibits the sphincter 18 from closing. When the generally closed end 5 of the distal segment 2 reaches the bladder 15, fluid flows through the stent 1 and delivery catheter 20' indicating the target organ and/or body cavity, such as, for example, the bladder 15 has been reached.

Thereafter, the proximal release structure 26 is removed and the delivery catheter 20' is used to advance the elongated distal segment 2" further upwards relative to the bladder 15 to extend the flexible connecting structure 4 within the region of the anatomical constricting structure, such as, for example, the sphincter 18. Thus, it should be appreciated that the delivery catheter 20' moves through the proximal segment 3" as the delivery catheter 20' is advanced further into the urethra 19. Then the distal release structure 28 is removed.

Next, the first and second tubular segments 22' and 24' of the delivery catheter 20' are removed. The flexible connecting structure 4 may be manipulated to a more appropriate position within the anatomical constricting structure, such as, for example, the sphincter 18, by gently pulling on the at least one withdrawal threads, pull-wires, or other equivalent structures 8.

Finally, the stiff member 29 is removed leaving the stent 1 appropriately positioned within the anatomical constricting structure, such as, for example, the sphincter 18 to comply with the naturally occurring actions of the sphincter 18. However, it should be appreciated that the stiff member 29 could be removed earlier in the process.

It should be appreciated that seating of the flexible connecting structure 4 or 14 in any of the embodiments described related to FIGS. 26–31 need not require an elongated distal segment 2" provided that a sufficiently long flexible connecting structure 4 or 14 is used. As in earlier described embodiments, the connecting structure 4 or 14 joins the distal and proximal segments 2 and 3. As the stent 1 is inserted into the anatomical tract, such as, for example, the urethra 19, the length of the flexible connecting structure 4 or 14 permits the proximal segment 3 to remain entirely below the anatomical constricting structure, such as, for example, the sphincter 18.

Then, either the distal segment 2 is manipulated further upward relative to the target organ and/or body cavity to extend the flexible connecting structure 4 or 14 in the anatomical constricting structure, such as, for example, the sphincter 18, or the proximal segment 3 is manipulated downward relative to the anatomical constricting structure, such as, for example, the sphincter 18 to extend the flexible connecting structure 4 or 14 across the anatomical constricting structure, such as, for example, the sphincter 18.

In either case, the flexible connecting structure 4 or 14 may be more specifically positioned within the anatomical constricting structure, such as, for example, the sphincter 18 by gently tugging on the withdrawal threads, pull-wires, or other equivalent structures 8 so that the stent 1 complies with the naturally occurring functions of the sphincter 18.

It should be appreciated that in all of the exemplary embodiments requiring a stiff member 29, the stiff member 29 may be blunted or otherwise shaped on the end of the stiff member 29 that contacts the closed rounded end of the distal segment. The blunting or otherwise shaped end of stiff member 29 may prevent the "spearing" of the closed rounded end 5 of the distal stent segment 2. The blunting or otherwise shaped end of stiff member 29 may also prevent the stiff member from accidentally protruding through the opening 6 of the distal stent segment 2.

Still further, it should be appreciated that all of the embodiments described herein are exemplary only and that this invention, including the stent 1, and methods of inserting and withdrawing the stent 1 from an anatomical tract of a living being may also be used to instill fluids, or other irrigating solutions, to a target body cavity or organ as well rather than for the exemplary described purpose of emptying or eliminating fluids from, for example, a target organ or body cavity of a living being. Further, it should be appreciated that the invention may also be used to insert or control other instruments, e.g., an endoscope, to view, or otherwise involve, a target body cavity or organ by deploying an instrument through the assembly 100, 200 or 300 and stent 1 using the methods and devices herein described.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A method of placing a prosthesis into an anatomical tract that passes through an anatomical constricting structure, the prosthesis comprising a first segment, a second segment and a connection structure that flexibly connects the first and second segments, the prosthesis mounted on an insertion assembly, the method comprising:

inserting the prosthesis and the insertion assembly into an opening in the anatomical tract;

advancing the prosthesis through the anatomical tract using the insertion assembly until at least the first segment is at least partially located on a far side of the anatomical constricting structure from the opening in the anatomical tract;

at least partially withdrawing at least a first portion of the insertion assembly from the anatomical tract relative to the prosthesis; and manipulating at least one of (a) a second portion of the insertion assembly and (b) a portion of the prosthesis to extend the connection structure through the anatomical constricting structure, the first segment being located entirely on the far side of the anatomical constricting structure, and the second segment being located entirely on a near side of the anatomical constricting structure relative to the opening in the anatomical tract.

2. The method of claim 1, wherein advancing the prosthesis through the anatomical tract using the insertion assembly comprises locating at least one of the first and second segments relative to at least one of an organ and a cavity associated with the anatomical tract.

3. The method of claim 2, wherein locating at least one of the first and second segments relative to at least one of an organ and a cavity comprises locating the first segment relative to an opening in a bladder.

4. The method of claim 3, wherein:

the first segment comprises a first end connected to the connection structure and a second end opposite the first end, the second end having an opening; and locating the first segment relative to the opening in the bladder comprises advancing the second end of the first segment through the opening in the bladder and into the bladder such that fluid held in the bladder can flow through the opening of the second end and into the first segment.

5. The method of claim 4, wherein:

the insertion assembly comprises:

a mandrel, a pusher mountable on the mandrel, and a removal structure attached to one of the first and second segments; and at least partially withdrawing at least a portion of the insertion assembly from the anatomical tract comprises removing the mandrel and the pusher from the anatomical constricting structure.

6. The method of claim 5, wherein locating the first segment relative to the at least one of an organ and a cavity comprises locating the first segment entirely on the far side of the anatomical constricting structure.

7. The method of claim 6, wherein manipulating one of the second portion of the insertion assembly and a portion of the prosthesis comprises pulling on at least a portion of the removal structure until the connection structure extends through the anatomical constricting structure and the second segment is entirely on the near side.

8. The method of claim 2, wherein:

the first segment comprises a first end connected to the connection structure and a second end opposite the first end, the second end having an opening; and locating the first segment relative to the organ and/or cavity comprises advancing the second end of the first segment through an opening in the organ and/or cavity and into the organ and/or cavity such that at least one of liquids and gases flow through the prosthesis signaling entry of the first segment into the organ and/or cavity.

9. The method of claim 2, wherein locating at least one of the first and second segments relative to at least one of the organ and the cavity comprises advancing the first segment entirely through the anatomical constricting structure and advancing the second segment at most partially through the anatomical constricting structure.

10. The method of claim 9, wherein:

the insertion assembly comprises:

a mandrel;

a pusher mountable on the mandrel;

a removal structure attached to one of the first and second segments; and at least partially withdrawing at least a portion of the insertion assembly from the anatomical tract comprises removing the mandrel and the pusher from the anatomical constricting structure.

11. The method of claim 10, wherein manipulating one of the second portion of the insertion assembly and a portion of the prosthesis comprises pulling on at least a portion of the removal structure until the connection structure extends through the anatomical constricting structure and the second segment is on the near side.

12. The method of claim 9, wherein manipulating one of the second portion of the insertion assembly and a portion of the prosthesis comprises pulling one of the second portion of the insertion assembly and a portion of the prosthesis to withdraw the second segment to the near side such that the connection structure extends through the anatomical constricting structure.

13. The method of claim 12, wherein said pulling comprises pulling at least a portion of a removal structure, the pulled portion of the removal structure attached to at least the second segment.

14. The method of claim 13, wherein the pulled portion of the removal structure includes at least a removal thread attached to the second segment.

15. The method of claim 12, wherein:
the insertion assembly comprises:
a mandrel,
a pusher mountable on the mandrel, and
a removal structure attached to one of the first and second segments; and
at least partially withdrawing at least a portion of the insertion assembly from the anatomical tract comprises removing the mandrel and the pusher from the anatomical constricting structure.

16. The method of claim 15, wherein pulling the second portion of the insertion assembly comprises pulling at least a portion of the removal structure that is attached to the second segment.

17. The method of claim 12, wherein:
the insertion assembly comprises:
a stiff member that extends through the first and second segments and the connection structure and that contacts an end of the first segment that is opposite an end of the first segment connected to the connection structure,
an insertion structure that extends through the second segment and the connection structure and into the first segment,
at least one segment release structure, each segment release structure releasably connecting the insertion structure to one of the first and second segments, and
a removal structure attached to at least the second segment; and
pulling at least one of the second portion of the insertion assembly and the portion of the prosthesis comprises pulling the insertion structure.

18. The method of claim 17, wherein:
the at least one segment release structure comprises a first segment release structure that releasably connects the insertion structure to the first segment; and
withdrawing at least a portion of the insertion assembly comprises withdrawing the first segment release structure to release the first segment from the insertion structure before pulling the insertion structure.

19. The method of claim 17, wherein withdrawing at least a portion of the insertion assembly further comprises at least partially withdrawing the stiff member from the prosthesis before pulling the insertion structure.

20. The method of claim 17, further comprising, after pulling the insertion structure, withdrawing the stiff member from the anatomical tract.

21. The method of claim 20, further comprising, after removing the stiff member, withdrawing the insertion structure from the anatomical tract.

22. The method of claim 21, wherein:
when the first and second segments and the connection structure are mounted on the insertion structure, the at least one segment release structure releasably connects the insertion structure to the first and second segments such that the connection structure is in a collapsed state; and
pulling the insertion structure after withdrawing the segment release structure that connects the insertion structure to the first segment causes the connection structure to expand from the collapsed state and extend through the anatomical constricting structure.

23. The method of claim 17, wherein withdrawing at least a portion of the insertion assembly further comprises withdrawing one of the at least one segment release structure that connects the insertion structure to the first segment before pulling the insertion structure.

24. The method of claim 23, wherein the at least one segment release structure further releasably connects the insertion structure to the first and second segments such that the first and second segments approximately abut each other.

25. The method of claim 17, wherein the stiff member contacts the first segment at a closed end of the first segment opposite an end of the first segment connected to the connection structure.

26. The method of claim 25, wherein at least partially withdrawing at least a portion of the insertion assembly from the anatomical tract relative to the prosthesis further comprises at least partially withdrawing the stiff member from the prosthesis before partially withdrawing the insertion structure from the anatomical tract.

27. The method of claim 26, further comprising withdrawing the stiff member from the anatomical tract.

28. The method of claim 27, wherein the at least one segment release structure releasably further connects the insertion structure to the first and second segments such that the first and second segments approximately abut each other.

29. The method of claim 25, further comprising, after partially withdrawing the insertion structure from the anatomical tract:
removing the second segment release structure from the insertion assembly to release the second segment from the insertion structure; and
withdrawing the insertion structure from the anatomical tract.

30. The method of claim 29, wherein:
when the first and second segments and the connection structure are mounted on the insertion structure, the at least one segment release structure releasably connects the insertion structure to the first and second segments such that the connection structure is in a collapsed state; and
pulling the insertion structure after withdrawing the segment release structure that connects the insertion structure to the first segment causes the connection structure to expand from the collapsed state and extend through the anatomical constricting structure.

31. The method of claim 12, wherein:
the insertion assembly comprises:
a stiff member that extends through the first and second segments and the connection structure and that contacts the first segment,
an insertion structure that extends through the second segment and the connection structure and into the first segment,
a first segment release structure that releasably holds the first segment relative to the insertion structure, and
a second segment release structure that releasably holds the second segment relative to the insertion structure;
at least partially withdrawing at least a portion of the insertion assembly from the anatomical tract relative to the prosthesis comprises removing the first segment release structure from the insertion assembly to release the first segment from the insertion structure; and
pulling at least one of the second portion of the insertion assembly and the portion of the prosthesis comprises partially withdrawing the insertion structure from the anatomical tract.

32. The method of claim 2, wherein:
locating at least one of the first and second segments relative to at least one of the organ and the cavity comprises advancing the first segment at most partially through the anatomical constricting structure; and manipulating one of the second portion of the insertion assembly and a portion of the prosthesis comprises advancing the second portion of the insertion assembly further into the anatomical tract to advance the first segment entirely to the far side of the anatomical constricting structure such that the connection structure extends through the anatomical constricting structure.

33. The method of claim 32, wherein:
the insertion assembly comprises:
a stiff member that extends through the first and second segments and the connection structure and that contacts the first segment,
a first portion of the insertion assembly that extends through the second segment and the connection structure and into the first segment,
a first segment release structure that releasably holds the first segment relative to the insertion assembly, and
a second segment release structure that releasably holds the second segment relative to the insertion assembly; and
at least partially withdrawing at least a first portion of the insertion assembly from the anatomical tract relative to the prosthesis comprises removing the first segment release structure from the insertion assembly to release the first segment from the insertion structure; and
advancing the second portion of the insertion assembly comprises advancing the stiff member to advance the first segment entirely to the far side of the anatomical constricting structure.

34. The method of claim 33, wherein:
when the first and second segments and the connection structure are mounted on the insertion structure, the at least one segment release structure releasably connects the insertion structure to the first and second segments such that the connection structure is in a collapsed state; and
advancing the insertion structure after withdrawing the segment release structure that connects the insertion structure to the first segment causes the connection structure to expand from the collapsed state and extend through the anatomical constricting structure.

35. The method of claim 33, wherein the at least one segment release structure further releasably connects the insertion assembly to the first and second segments such that the first and second segments approximately abut each other.

36. The method of claim 32, wherein advancing the second portion of the insertion assembly comprises advancing the second portion to place the first segment in a location on the far side of the anatomical constricting structure that is relative to at least one of an organ and a cavity associated with the anatomical tract.

37. The method of claim 36, wherein placing the first segment in a location relative to at least one of an organ and a cavity comprises placing the first segment relative to an opening in a bladder.

38. The method of claim 37, wherein:
the first segment comprises a first end connected to the connection structure and a second end opposite the first end, the second end having an opening; and
placing the first segment relative to the opening in the bladder comprises advancing the second end of the first segment through the opening and into the bladder such that fluid held in the bladder can flow into the first segment.

39. The method of claim 32, wherein:
the insertion assembly comprises:
a stiff member that extends through the first and second segments and the connection structure and that contacts the first segment,
an insertion structure that extends through the second segment and the connection structure and into the first segment,
a first segment release structure that releasably holds the first segment relative to the insertion structure, and
a second segment release structure that releasably holds the second segment relative to the insertion structure;
at least partially withdrawing at least a first portion of the insertion assembly from the anatomical tract relative to the prosthesis comprises removing the second segment release structure from the insertion assembly to release the second segment from the insertion structure;
advancing the second portion of the insertion assembly comprises advancing the insertion structure to advance the first segment entirely to the far side of the anatomical constricting structure.

40. The method of claim 39, wherein:
when the first and second segments and the connection structure are mounted on the insertion structure, the at least one segment release structure releasably connects the insertion structure to the first and second segments such that the connection structure is in a collapsed state; and
advancing the insertion structure after withdrawing the segment release structure that connects the insertion structure to the second segment causes the connection structure to expand from the collapsed state and extend through the anatomical constricting structure.

41. The method of claim 40, wherein the at least one segment release structure further releasably connects the insertion structure to the first and second segments such that the first and second segments approximately abut each other.

42. The method of claim 39, further comprising:
removing the first segment release structure from the insertion structure; and
removing the insertion structure from the anatomical tract.

43. The method of claim 39, wherein advancing the second portion of the insertion assembly comprises advancing the second portion to place the first segment in a location on the far side of the anatomical constricting structure that is relative to at least one of an organ and a cavity associated with the anatomical tract.

44. The method of claim 43, wherein placing the first segment in a location relative to at least one of an organ and a cavity comprises placing the first segment relative to an opening in a bladder.

45. The method of claim 44, wherein:
the first segment comprises a first end connected to the connection structure and a second end opposite the first end, the second end having an opening; and
placing the first segment relative to the opening in the bladder comprises advancing the second end of the first segment through the opening and into the bladder such that fluid held in the bladder can flow into the first segment.

46. The method of claim 1, wherein:
locating the first segment entirely on the far side of the anatomical constricting structure, and locating the second segment entirely on a near side of the anatomical constricting structure relative to the opening in the anatomical tract signals placement of the connecting structure within the anatomical constricting structure by voluntary control of the anatomical constricting structure.

* * * * *